(12) United States Patent
Ueda et al.

(10) Patent No.: US 8,383,363 B1
(45) Date of Patent: *Feb. 26, 2013

(54) L-AMINO ACID-PRODUCING MICROORGANISM AND METHOD FOR PRODUCING L-AMINO ACID

(75) Inventors: Takuji Ueda, Kawasaki (JP); Yuta Nakai, Kawasaki (JP); Yoshiya Gunji, Kawasaki (JP); Rie Takikawa, Kawasaki (JP); Yuji Joe, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 409 days.

This patent is subject to a terminal disclaimer.

(21) Appl. No.: 11/759,419

(22) Filed: Jun. 7, 2007

Related U.S. Application Data

(63) Continuation of application No. 11/044,347, filed on Jan. 28, 2005.

(30) Foreign Application Priority Data

Jan. 30, 2004 (JP) ................................ 2004-023347

(51) Int. Cl.
  C12P 1/00 (2006.01)
  C12P 1/04 (2006.01)
  C12P 13/08 (2006.01)
  C12P 13/10 (2006.01)
(52) U.S. Cl. ......... 435/41; 435/69.1; 435/114; 435/115; 435/106
(58) Field of Classification Search .................. None
  See application file for complete search history.

(56) References Cited

U.S. PATENT DOCUMENTS

| | | | |
|---|---|---|---|
| 5,939,307 A * | 8/1999 | Wang et al. .............. 435/252.33 |
| 5,972,663 A | 10/1999 | Winterhalter et al. | |
| 6,303,348 B1 | 10/2001 | Livshits et al. | |
| 6,410,705 B1 | 6/2002 | Ziegler et al. | |
| 6,451,564 B1 | 9/2002 | Guillouet et al. | |
| 6,858,406 B1 | 2/2005 | Vrlijc et al. | |
| 6,861,246 B2 | 3/2005 | Kreutzer et al. | |
| 6,962,805 B2 * | 11/2005 | Asakura et al. .............. 435/110 |
| 7,049,106 B2 | 5/2006 | Farwick et al. | |
| 7,144,724 B2 | 12/2006 | Farwick et al. | |
| 7,169,587 B2 | 1/2007 | Gunji et al. | |
| 7,211,416 B2 | 5/2007 | Asahara et | |
| 7,217,543 B2 | 5/2007 | Gunji et al. | |
| 7,223,572 B1 | 5/2007 | Gunji et al. | |
| 2002/0022718 A1 * | 2/2002 | Forsyth et al. .............. 536/23.1 |
| 2002/0106800 A1 * | 8/2002 | Liaw et al. .................. 435/488 |
| 2002/0160461 A1 | 10/2002 | Nakai et al. | |
| 2003/0148473 A1 | 8/2003 | Livshits et al. | |
| 2003/0157667 A1 | 8/2003 | Vitushkina et al. | |
| 2004/0014123 A1 | 1/2004 | Kennerknecht et al. | |
| 2004/0029129 A1 | 2/2004 | Wang et al. | |
| 2004/0121428 A1 | 6/2004 | Sugimoto et al. | |
| 2004/0142435 A1 | 7/2004 | Gunji et al. | |
| 2004/0146974 A1 | 7/2004 | Gunji et al. | |
| 2004/0265956 A1 | 12/2004 | Takikawa et al. | |
| 2005/0003495 A1 | 1/2005 | Gunji et al. | |
| 2005/0176121 A1 | 8/2005 | Takeshita et al. | |
| 2005/0260720 A1 | 11/2005 | Ito et al. | |
| 2005/0277179 A1 | 12/2005 | Takai et al. | |
| 2006/0088919 A1 | 4/2006 | Rybak et al. | |
| 2006/0154344 A1 | 7/2006 | Van Dien et al. | |
| 2006/0160191 A1 | 7/2006 | Kataoka et al. | |
| 2006/0216796 A1 | 9/2006 | Hashiguchi et al. | |
| 2007/0004014 A1 | 1/2007 | Tsuji et al. | |

FOREIGN PATENT DOCUMENTS

| | | |
|---|---|---|
| EP | 1 013 765 | 6/2000 |
| EP | 1 016 710 | 7/2000 |
| EP | 1 033 407 A1 * | 9/2000 |
| EP | 1 094 107 | 4/2001 |
| EP | 1 239 041 | 9/2002 |
| EP | 1 266 966 | 12/2002 |
| EP | 1 574 582 | 9/2005 |
| KR | 20010049728 | 6/2001 |
| KR | 20040014489 | 2/2004 |
| WO | 97/23597 | 7/1997 |
| WO | WO 98/04715 * | 2/1998 |
| WO | WO 99/46363 * | 9/1999 |
| WO | 00/77172 | 12/2000 |
| WO | 01/53459 | 7/2001 |
| WO | 03/014330 | 2/2003 |
| WO | 2004/087937 | 10/2004 |

OTHER PUBLICATIONS

Ciccarelli FD et al., (2006). "Toward automatic reconstruction of a highly resolved tree of life". Science 311 (5765): 1283-7.*

Spiro et al., 1990; FNR and Its Role in Oxygen-Regulated Gene Expressi from FEMS Microbiology Reviews pp. 399-428.*

McAdams et al., It's a noisy business! Gentic regulation at the nanomolar scale. Trends in Genetics 1999; pp. 65-69.*

Verrey et al., 2000 Glycoprotein-associated amino acid exchangers: broadening the range of transport specificity Eur J Physiolo 503-512.*

Kennell, Principles and practices of nucleic acid hybridization. Progr. Nucleic Acid Res. Mol. Biol. 11: 259-301, 1971.*

SCORE Search Results Details for U.S. Appl. No. 11/759,419 and Search Result 20091110__134959__us-11-759-419-2.rag.*

Bork Power and Pitfalls in Sequence Analysis: The 70% Hurdle Genome Research 10:398-400 (2000).*

Rudinger, J., "Characteristics of the amino acids as components of a peptide hormone sequence",in Peptide Hormones, University Park Press: Baltimore, MD, pp. 1-7, 1976.*

(Continued)

*Primary Examiner* — Maria Leavitt

(74) *Attorney, Agent, or Firm* — Shelly Guest Cermak; Cermak Nakajima LLP

(57) ABSTRACT

L-amino acids are produced by culturing a microorganism which has an ability to produce the L-amino acid, but has been modified so that expression of the ybjE gene has been enhanced. The L-amino acid is collected from the culture medium or from the microorganism.

10 Claims, 16 Drawing Sheets

OTHER PUBLICATIONS

Bowie et al., Deciphering the message in protein sequences: tolerance to amino acid substitutions.Science. 1990 ;247:1306-10.*

Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-495.*

Goldstein et al., Biotechnolgy Annual Review vol. 1 pp. 105-128.*

Boer et al., Proc. Natl. Acad. Sci. 1983, pp. 21-25.*

Blattner et al., Science. Sep. 5, 1997;277(5331):1453-62. The complete genome sequence of *Escherichia coli* K-12.*

Bellmann et al., Expression control and specificity of the basic amino acid exporter LysE of *Corynebacterium glutamicum* Microbiology 147 (2001), 1765-1774.*

Biochemistry, John Wiley and Sons, 1990, pp. 126-129.

Blattner, F.R., et al., "The Complete Genome Sequence of *Escherichia coli* K-12," Science 1997;277(5):1453-1462.

Cruz-Ramos, H., et al., "Membrane topology and mutational analysis of *Escherichia coli* CydDC, an ABC-type cysteine exporter required for cytochrome assembly," Microbiology 2004;150:3415-3427.

Cummings, L., "Genomic BLAST: custom-defined virtual databases for complete and unfinished genomes," FEMS Microbiol. Lett. 2002;216(2):133-138.

DATABASE EPO Protein 'Online!, Aug. 8, 2001, "Sequence 361 from Patent WO0148209." XP002328532 retrieved from EBI accession No. EPOP: AX189160, Database accession No. AX189160.

DATABASE Geneseq 'Online!, Sep. 21, 2001, "*Escherichia coli* protein encoding nucleotide sequence SEQ ID No: 168." XP00328531 retrieved from EBI accession No. GSN: AAH81369. Database accession No. AAH81369.

Gunji, Y., et al., "Characterization of the L-lysine biosynthetic pathway in the obligate methylotroph Methylophilus methylotrophus," Biosci. Biotechnol. Biochem. 2004;68(7):1449-1460.

Imaizumi, A., et al., "Improved production of L-lysine by disruption of stationary phase-specific rmf gene in *Escherichia coli*," J. Biotechnol. 2005;117(1):111-118.

Mims et al., Medical Microbiology, Third Edition, Elsevier Science, 2004, pp. 280-282.

Nandineni, M. R., et al., "Evidence for an Arginine Exporter Encoded by *yggA* (*argO*) That Is Regulated by the LysR-Type transcriptional Regulator ArgP in *Escherichia coli*," J. Bacteriol. 2004;186(11):3539-3546.

NCBI genomic BLAST with microbial genomes, pp. 1-11.

Perna, N. T., et al., "Genome sequence of enterohaemorrhagic *Escherichia coli* O157:H7," Nature 2001;409(6819):529-533. Erratum in: Nature 2001 410(6825):240.

Recombinant DNA, Second edition, Watson et al., 2001, pp. 49-50.

See SORE. Result 2, p. 1-3, on the attached search print out titled us 11-044-347b-1.n2p.rapm. pp. 1-3.

STIC Protein Search Report. Tracking No. 11-044-347, pp. 1-17.

Vrljic, M., et al., "The LysE Superfamily: Topology of the Lysine Exporter LysE of *Corynebacterium glutamicum*, a Paradyme for a Novel Superfamily of Transmembrane Solute Translocators," J. Mol. Microbiol. Biotechnol. 1999;1(1):327-336.

ybhE Genbank, Definition: putative membrane protein [*Escherichia coli* K12], Accession: No. 415395, Version: NP_415395.1; GI: 16128842.

Zakataeva, N. P., et al., "The novel tranmembrane *Escherichia coli* proteins involved in the amino acid efflux," FEBS Letters 1999;452:228-232.

International Search Report for PCT Patent App. No. PCT/JP2005/001650 (Jun. 3, 2005).

Notice of Patent Grant for co-pending Korean Patent App. No. 10-2006-7006905 and English translation thereof.

U.S. Appl. No. 60/644,040, filed Jan. 18, 2005, Kataoka et al.

U.S. Appl. No. 60/673,338, filed Apr. 21, 2005, Kataoka et al.

U.S. Appl. No. 60/695,846, filed Jul. 5, 2005, Tsuji et al.

U.S. Appl. No. 11/563,289, filed Nov. 27, 2006, Gunji et al.

U.S. Appl. No. 11/738,617, filed Apr. 23, 2007, Gunji et al.

* cited by examiner

SEQUENCE LISTING

```
<160> NUMBER OF SEQ ID NOS: 17

<210> SEQ ID NO 1
<211> LENGTH: 948
<212> TYPE: DNA
<213> ORGANISM: Escherichia coli
<220> FEATURE:
<221> NAME/KEY: CDS
<222> LOCATION: (1)..(948)
<223> OTHER INFORMATION:

<400> SEQUENCE: 1 gtg tgt cat cgc gca ttt cga ctt cat ctt tgc aag gac tgg gtt ttc      48
Val Cys His Arg Ala Phe Arg Leu His Leu Cys Lys Asp Trp Val Phe
1               5                   10                  15 atg ttt tct ggg ctg tta atc att ctg gtt ccc ctg att gtg ggt tac      96
Met Phe Ser Gly Leu Leu Ile Ile Leu Val Pro Leu Ile Val Gly Tyr
            20                  25                  30 ctc att ccg ctt cgc caa caa gct gcg tta aaa gtt att aat cag cta     144
Leu Ile Pro Leu Arg Gln Gln Ala Ala Leu Lys Val Ile Asn Gln Leu
        35                  40                  45 tta agc tgg atg gtt tac ctt att ctc ttt ttt atg ggt atc agt ctg     192
Leu Ser Trp Met Val Tyr Leu Ile Leu Phe Phe Met Gly Ile Ser Leu
    50                  55                  60 gcg ttt ctc gat aac ctc gcc agt aac ctg ttg gcg att ctg cat tat     240
Ala Phe Leu Asp Asn Leu Ala Ser Asn Leu Leu Ala Ile Leu His Tyr
65                  70                  75                  80 tct gcc gtc agt att acc gtt att tta ctg tgt aat att gcc gcc ctg     288
Ser Ala Val Ser Ile Thr Val Ile Leu Leu Cys Asn Ile Ala Ala Leu
```

|    |    |    |    |    |    |    |    |    |    |    |    |    |    |    |    |     |
|----|----|----|----|----|----|----|----|----|----|----|----|----|----|----|----|-----|
|    |    |    |    | 85 |    |    |    |    | 90 |    |    |    |    | 95 |    |     |
| atg | tgg | ctg | gag | cga | ggc | ctg | ccg | tgg | cgc | aac | cac | cat | cag | caa | gaa | 336 |
| Met | Trp | Leu | Glu | Arg | Gly | Leu | Pro | Trp | Arg | Asn | His | His | Gln | Gln | Glu |     |
|    |    |    | 100 |    |    |    |    | 105 |    |    |    |    | 110 |    |    |     |
| aaa | ctc | ccg | tcg | cgt | att | gcg | atg | gcg | ctg | gag | tcg | cta | aaa | ctg | tgc | 384 |
| Lys | Leu | Pro | Ser | Arg | Ile | Ala | Met | Ala | Leu | Glu | Ser | Leu | Lys | Leu | Cys |     |
|    |    |    | 115 |    |    |    |    | 120 |    |    |    |    | 125 |    |    |     |
| ggc | gta | gta | gtg | att | ggt | ttt | gcc | att | ggt | cta | agt | gga | ctg | gct | ttc | 432 |
| Gly | Val | Val | Val | Ile | Gly | Phe | Ala | Ile | Gly | Leu | Ser | Gly | Leu | Ala | Phe |     |
|    |    | 130 |    |    |    |    | 135 |    |    |    |    | 140 |    |    |    |     |
| tta | caa | cac | gcg | acc | gaa | gcc | agt | gaa | tac | acg | tta | att | ttg | cta | ctt | 480 |
| Leu | Gln | His | Ala | Thr | Glu | Ala | Ser | Glu | Tyr | Thr | Leu | Ile | Leu | Leu | Leu |     |
| 145 |    |    |    |    | 150 |    |    |    |    | 155 |    |    |    |    | 160 |     |
| ttc | ctc | gtt | ggt | att | cag | ttg | cgc | aat | aat | ggc | atg | acc | tta | aag | cag | 528 |
| Phe | Leu | Val | Gly | Ile | Gln | Leu | Arg | Asn | Asn | Gly | Met | Thr | Leu | Lys | Gln |     |
|    |    |    |    | 165 |    |    |    |    | 170 |    |    |    |    | 175 |    |     |
| att | gtc | ctt | aat | cgc | cgg | gga | atg | att | gtc | gcc | gtg | gtg | gtg | gtt | gtc | 576 |
| Ile | Val | Leu | Asn | Arg | Arg | Gly | Met | Ile | Val | Ala | Val | Val | Val | Val | Val |     |
|    |    |    | 180 |    |    |    |    | 185 |    |    |    |    | 190 |    |    |     |
| agt | tca | tta | att | ggt | ggt | tta | att | aac | gcc | ttt | att | ctt | gat | ctc | ccc | 624 |
| Ser | Ser | Leu | Ile | Gly | Gly | Leu | Ile | Asn | Ala | Phe | Ile | Leu | Asp | Leu | Pro |     |
|    |    |    | 195 |    |    |    |    | 200 |    |    |    |    | 205 |    |    |     |
| atc | aat | acc | gcg | ctg | gca | atg | gcc | tcc | ggt | ttc | ggc | tgg | tat | tct | ctt | 672 |
| Ile | Asn | Thr | Ala | Leu | Ala | Met | Ala | Ser | Gly | Phe | Gly | Trp | Tyr | Ser | Leu |     |
|    |    | 210 |    |    |    |    | 215 |    |    |    |    | 220 |    |    |    |     |
| tcc | ggt | att | tta | ttg | acc | gaa | tct | ttt | ggt | ccg | gta | atc | ggg | agc | gcg | 720 |
| Ser | Gly | Ile | Leu | Leu | Thr | Glu | Ser | Phe | Gly | Pro | Val | Ile | Gly | Ser | Ala |     |
| 225 |    |    |    |    | 230 |    |    |    |    | 235 |    |    |    |    | 240 |     |
| gcg | ttt | ttt | aat | gat | ctg | gcc | cgt | gaa | ctg | att | gct | att | atg | ttg | atc | 768 |
| Ala | Phe | Phe | Asn | Asp | Leu | Ala | Arg | Glu | Leu | Ile | Ala | Ile | Met | Leu | Ile |     |
|    |    |    |    | 245 |    |    |    |    | 250 |    |    |    |    | 255 |    |     |
| cct | ggg | ctg | att | cgc | cgc | agc | cgc | tct | act | gca | ctg | ggc | tta | tgc | ggt | 816 |
| Pro | Gly | Leu | Ile | Arg | Arg | Ser | Arg | Ser | Thr | Ala | Leu | Gly | Leu | Cys | Gly |     |
|    |    |    | 260 |    |    |    |    | 265 |    |    |    |    | 270 |    |    |     |
| gcc | aca | tca | atg | gat | ttc | acc | ctg | ccc | gtt | ctt | caa | cgt | act | ggc | ggg | 864 |
| Ala | Thr | Ser | Met | Asp | Phe | Thr | Leu | Pro | Val | Leu | Gln | Arg | Thr | Gly | Gly |     |
|    |    | 275 |    |    |    |    | 280 |    |    |    |    | 285 |    |    |    |     |
| ctg | gat | atg | gtc | ccg | gcg | gca | att | gtt | cac | ggt | ttt | att | ctt | agc | ctg | 912 |
| Leu | Asp | Met | Val | Pro | Ala | Ala | Ile | Val | His | Gly | Phe | Ile | Leu | Ser | Leu |     |
|    | 290 |    |    |    |    | 295 |    |    |    |    | 300 |    |    |    |    |     |
| tta | gtg | ccg | atc | ctc | atc | gcc | ttt | ttc | tct | gcg | taa |    |    |    |    | 948 |
| Leu | Val | Pro | Ile | Leu | Ile | Ala | Phe | Phe | Ser | Ala |    |    |    |    |    |     |
| 305 |    |    |    | 310 |    |    |    |    | 315 |    |    |    |    |    |    |     |

<210> SEQ ID NO 2
<211> LENGTH: 315
<212> TYPE: PRT
<213> ORGANISM: Escherichia coli

<400> SEQUENCE: 2

| Val | Cys | His | Arg | Ala | Phe | Arg | Leu | His | Leu | Cys | Lys | Asp | Trp | Val | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Met | Phe | Ser | Gly | Leu | Leu | Ile | Ile | Leu | Val | Pro | Leu | Ile | Val | Gly | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Ile | Pro | Leu | Arg | Gln | Gln | Ala | Ala | Leu | Lys | Val | Ile | Asn | Gln | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Leu | Ser | Trp | Met | Val | Tyr | Leu | Ile | Leu | Phe | Phe | Met | Gly | Ile | Ser | Leu |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Ala | Phe | Leu | Asp | Asn | Leu | Ala | Ser | Asn | Leu | Leu | Ala | Ile | Leu | His | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

```
Ser Ala Val Ser Ile Thr Val Ile Leu Leu Cys Asn Ile Ala Ala Leu
             85                  90                  95

Met Trp Leu Glu Arg Gly Leu Pro Trp Arg Asn His His Gln Gln Glu
        100                 105                 110

Lys Leu Pro Ser Arg Ile Ala Met Ala Leu Glu Ser Leu Lys Leu Cys
            115                 120                 125

Gly Val Val Val Ile Gly Phe Ala Ile Gly Leu Ser Gly Leu Ala Phe
        130                 135                 140

Leu Gln His Ala Thr Glu Ala Ser Glu Tyr Thr Leu Ile Leu Leu Leu
145                 150                 155                 160

Phe Leu Val Gly Ile Gln Leu Arg Asn Asn Gly Met Thr Leu Lys Gln
                165                 170                 175

Ile Val Leu Asn Arg Arg Gly Met Ile Val Ala Val Val Val Val Val
            180                 185                 190

Ser Ser Leu Ile Gly Gly Leu Ile Asn Ala Phe Ile Leu Asp Leu Pro
            195                 200                 205

Ile Asn Thr Ala Leu Ala Met Ala Ser Gly Phe Gly Trp Tyr Ser Leu
            210                 215                 220

Ser Gly Ile Leu Leu Thr Glu Ser Phe Gly Pro Val Ile Gly Ser Ala
225                 230                 235                 240

Ala Phe Phe Asn Asp Leu Ala Arg Glu Leu Ile Ala Ile Met Leu Ile
                245                 250                 255

Pro Gly Leu Ile Arg Arg Ser Arg Ser Thr Ala Leu Gly Leu Cys Gly
            260                 265                 270

Ala Thr Ser Met Asp Phe Thr Leu Pro Val Leu Gln Arg Thr Gly Gly
            275                 280                 285

Leu Asp Met Val Pro Ala Ala Ile Val His Gly Phe Ile Leu Ser Leu
        290                 295                 300

Leu Val Pro Ile Leu Ile Ala Phe Phe Ser Ala
305                 310                 315

<210> SEQ ID NO 3
<211> LENGTH: 24
<212> TYPE: DNA
<213> ORGANISM: Artificial
<220> FEATURE:
<223> OTHER INFORMATION: primer

<400> SEQUENCE: 3
cgccagggtt ttcccagtca cgac                                          24

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
gagcggataa caatttcaca cagg                                          24

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
```

```
ggctctggcg aacaaaatcg                                              20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gccggagtac ggatagtttg                                              20

<210> SEQ ID NO 7
<211> LENGTH: 56
<212> TYPE: DNA
<213> ORGANISM: Artificial
<220> FEATURE:
<223> OTHER INFORMATION: primer

<400> SEQUENCE: 7
ataaaaccgt gaacaattgc cgccgggacc atatcccagt gccaacatag taagcc      56

<210> SEQ ID NO 8
<211> LENGTH: 56
<212> TYPE: DNA
<213> ORGANISM: Artificial
<220> FEATURE:
<223> OTHER INFORMATION: primer

<400> SEQUENCE: 8
ggttacctca ttccgcttcg ccaacaagct gcgttacctg tggaacacct acatct      56

<210> SEQ ID NO 9
<211> LENGTH: 299
<212> TYPE: PRT
<213> ORGANISM: Artificial
<220> FEATURE:
<223> OTHER INFORMATION: synthetic DNA
<220> FEATURE:
<221> NAME/KEY: MISC_FEATURE
<222> LOCATION: (22),(23),(27),(28),(31),(36),(59),(62),(71),(81),(86),
      (91),(110), (117),(120),(127),(128),(142),(154),(169),(176),(180),
      (183),(193), (194),(235),(244),(270),(273)..(275),(292),(294)
<223> OTHER INFORMATION: Xaa=any amino acid residue

<400> SEQUENCE: 9

Met Phe Ser Gly Leu Leu Ile Ile Leu Val Pro Leu Ile Val Gly Tyr
1               5                   10                  15

Leu Ile Pro Leu Arg Xaa Xaa Ala Ala Leu Xaa Xaa Ile Asn Xaa Leu
            20                  25                  30

Leu Ser Trp Xaa Val Tyr Leu Ile Leu Phe Phe Met Gly Ile Ser Leu
        35                  40                  45

Ala Phe Leu Asp Asn Leu Ala Ser Asn Leu Xaa Ala Ile Xaa His Tyr
    50                  55                  60

Ser Ala Val Ser Ile Thr Xaa Ile Leu Leu Cys Asn Ile Ala Ala Leu
65                  70                  75                  80

Xaa Trp Leu Glu Arg Xaa Leu Pro Trp Arg Xaa His His Gln Gln Glu
                85                  90                  95

Lys Leu Pro Ser Arg Ile Ala Met Ala Leu Glu Ser Leu Xaa Leu Cys
            100                 105                 110

Gly Val Val Xaa Gly Phe Xaa Ile Gly Leu Ser Gly Leu Xaa Xaa
        115                 120                 125

Leu Gln His Ala Thr Glu Ala Ser Glu Tyr Thr Leu Ile Xaa Leu Leu
    130                 135                 140
```

```
Phe Leu Val Gly Ile Gln Leu Arg Asn Xaa Gly Met Thr Leu Lys Gln
145                 150                 155                 160

Ile Val Leu Asn Arg Arg Gly Met Xaa Val Ala Val Val Val Val Xaa
                165                 170                 175

Ser Ser Leu Xaa Gly Gly Xaa Ile Asn Ala Phe Ile Leu Asp Leu Pro
            180                 185                 190

Xaa Xaa Thr Ala Leu Ala Met Ala Ser Gly Phe Gly Trp Tyr Ser Leu
        195                 200                 205

Ser Gly Ile Leu Leu Thr Glu Ser Phe Gly Pro Val Ile Gly Ser Ala
            210                 215                 220

Ala Phe Phe Asn Asp Leu Ala Arg Glu Leu Xaa Ala Ile Met Leu Ile
225                 230                 235                 240

Pro Gly Leu Xaa Arg Arg Ser Arg Ser Thr Ala Leu Gly Leu Cys Gly
            245                 250                 255

Ala Thr Ser Met Asp Phe Thr Leu Pro Val Leu Gln Arg Xaa Gly Gly
                260                 265                 270

Xaa Xaa Xaa Val Pro Ala Ala Ile Val His Gly Phe Ile Leu Ser Leu
            275                 280                 285

Leu Val Pro Xaa Leu Xaa Ala Phe Phe Ser Ala
            290                 295

<210> SEQ ID NO 10
<211> LENGTH: 298
<212> TYPE: PRT
<213> ORGANISM: Artificial
<220> FEATURE:
<223> OTHER INFORMATION: synthetic DNA
<220> FEATURE:
<221> NAME/KEY: MISC_FEATURE
<222> LOCATION: (2),(10),(14),(21)..(28),(31),(32),(39),(55),(56),(60),
      (62),(63),(65)..(71),(74),(75),(77),(78),(81),(82),(86),
      (87),(90)..(92),(94),(97),(102),(103),(116),(117),(120),
      (121),(125)..(128),(131),(133)..(135),(138),(139),(142),
      (154),(159),(168),(169),(172),(175),(176),(178),(180),
      (183),(185),(187),(188),(190),(194),(196),(215),(216),
      (235),(242),(244),(246),(270),(274),(285),(290),(294)
<223> OTHER INFORMATION: Xaa=any amino acid residue

<400> SEQUENCE: 10

Met Xaa Ser Gly Leu Leu Ile Ile Leu Xaa Pro Leu Ile Xaa Gly Tyr
1               5                   10                  15

Leu Ile Pro Leu Xaa Xaa Xaa Xaa Xaa Xaa Xaa Ile Asn Xaa Xaa
            20                  25                  30

Leu Ser Trp Met Val Tyr Xaa Ile Leu Phe Phe Met Gly Ile Ser Leu
                35                  40                  45

Ala Phe Leu Asp Asn Leu Xaa Xaa Asn Leu Leu Xaa Ile Xaa Xaa Tyr
            50                  55                  60

Xaa Xaa Xaa Xaa Xaa Xaa Ile Leu Xaa Xaa Asn Xaa Xaa Ala Leu
65                  70                  75                  80

Xaa Xaa Leu Glu Arg Xaa Xaa Pro Trp Xaa Xaa Xaa His Xaa Gln Glu
                85                  90                  95

Xaa Leu Pro Ser Arg Xaa Xaa Met Ala Leu Glu Ser Leu Lys Leu Cys
            100                 105                 110

Gly Val Val Xaa Xaa Gly Phe Xaa Xaa Gly Leu Ser Xaa Xaa Xaa Xaa
                115                 120                 125

Leu Gln Xaa Ala Xaa Xaa Xaa Ser Glu Xaa Xaa Leu Ile Xaa Leu Leu
            130                 135                 140

Phe Leu Val Gly Ile Gln Leu Arg Asn Xaa Gly Met Thr Leu Xaa Gln
145                 150                 155                 160
```

Ile Val Leu Asn Arg Arg Gly Xaa Xaa Val Ala Xaa Val Val Xaa Xaa
                165                 170                 175

Ser Xaa Leu Xaa Gly Gly Xaa Ile Xaa Ala Xaa Xaa Leu Xaa Leu Pro
        180                 185                 190

Ile Xaa Thr Xaa Leu Ala Met Ala Ser Gly Phe Gly Trp Tyr Ser Leu
        195                 200                 205

Ser Gly Ile Leu Leu Thr Xaa Xaa Phe Gly Pro Val Ile Gly Ser Ala
    210                 215                 220

Ala Phe Phe Asn Asp Leu Ala Arg Glu Leu Xaa Ala Ile Met Leu Ile
225                 230                 235                 240

Pro Xaa Leu Xaa Arg Xaa Ser Arg Ser Thr Ala Leu Gly Leu Cys Gly
            245                 250                 255

Ala Thr Ser Met Asp Phe Thr Leu Pro Val Leu Gln Arg Xaa Gly Gly
            260                 265                 270

Leu Xaa Met Val Pro Ala Ala Ile Val His Gly Phe Xaa Leu Ser Leu
    275                 280                 285

Leu Xaa Pro Ile Leu Xaa Ala Phe Phe Ser
    290                 295

<210> SEQ ID NO 11
<211> LENGTH: 27
<212> TYPE: DNA
<213> ORGANISM: Artificial
<220> FEATURE:
<223> OTHER INFORMATION: primer

<400> SEQUENCE: 11
ggcatatgtg tcatcgcgca tttcgac                                27

<210> SEQ ID NO 12
<211> LENGTH: 27
<212> TYPE: DNA
<213> ORGANISM: Artificial
<220> FEATURE:
<223> OTHER INFORMATION: primer

<400> SEQUENCE: 12
ggctcgagtt acgcagagaa aaaggcg                                27

<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13
ggcatatgtt ttctgggctg tta                                    23

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 14
tgacctgcag gtttgcacag aggatggccc atgtt                       35

<210> SEQ ID NO 15
<211> LENGTH: 36
<212> TYPE: DNA

```
<213> ORGANISM: Artificial Sequence
<220> FEATURE:
<223> OTHER INFORMATION: Description of Artificial Sequence: primer

<400> SEQUENCE: 15
cattctagat ccctaaactt tacagcaaac cggcat                              36

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 16
agggaattcc ccgttctgga taatgttttt tgcgccgac                           39

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 17
cggatgcatc tagagttaac ctgcagggtg aaattgttat ccgctcacaa ttccacac      58
```

L-AMINO ACID-PRODUCING MICROORGANISM AND METHOD FOR PRODUCING L-AMINO ACID

This application claims priority under 35 U.S.C. §119 to Japanese Patent Application No. 2004-023347, filed Jan. 30, 2004, and under 35 U.S.C. §120 as a continuation to U.S. patent application Ser. No. 11/044,347, filed Jan. 28, 2005, the contents of both of which are incorporated by reference in their entireties. The Sequence Listing filed in the parent application on Oct. 4, 2005 is also hereby incorporated by reference in its entirety.

BACKGROUND OF THE INVENTION

1. Technical Field

The present invention relates to a method for producing an L-amino acid by fermentation using a microorganism. Specifically, the present invention relates to a method for producing L-amino acids such as L-lysine, L-arginine, L-ornithine, L-histidine, L-isoleucine, L-threonine, L-proline, L-phenylalanine, L-cysteine, and L-glutamic acid. These are industrially useful L-amino acids. Namely, L-lysine, L-threonine, L-isoleucine, and L-proline are useful as additives for animal feed, components of health food, and amino acid infusions. L-arginine and L-ornithine are useful as liver function-promoting agents, amino acid infusions, and components of comprehensive amino acid preparations. L-histidine is useful as a liver function-promoting agent and as a precursor of histamine. L-phenylalanine is useful as a precursor of sweeteners.

2. Background Art

L-amino acids are industrially produced by fermentation using microorganisms belonging to the genus Brevibacterium, Corynebacterium, Escherichia, or the like.

Methods for producing L-lysine have been reported in EP 0857784A, JP 11-192088A, WO00/53726, and WO96/17930. Methods for producing L-arginine have been reported in EP 0999267A, EP 1170358A, and JP 2002-017342A. In these reported methods, basic L-amino acid-producing bacteria strains were used, including strains separated from nature or artificially mutated strains thereof, and recombinant strains which have enhanced activity of a basic L-amino acid biosynthetic enzyme.

Furthermore, methods for producing L-amino acids from methanol, which is available for fermentation in large amounts for low cost, using a mutated or genetically-modified microorganism strain belonging to the genus Methylophilus or Methylobacillus have also been reported (WO00/61723 and JP 2001-120269A).

Methods of modifying uptake or export of L-amino acids in bacterial cells have been known to improve the L-amino acid-producing ability of the bacteria. Methods of modifying L-amino acid uptake include eliminating or decreasing uptake of an L-amino acid into cells to enhance L-amino acid-producing ability. Specifically, these methods include a method of deleting the gluABCD operon, or a part thereof, to eliminate or attenuate uptake of L-glutamic acid (EP 1038970A).

Methods of modifying exporter include eliminating or reducing export of an intermediate or a substrate of L-amino acid biosynthesis, and a method of enhancing export of a produced L-amino acid. As a method of eliminating or reducing export of an intermediate of L-glutamic acid biosynthesis, a method of mutating or disrupting α-ketoglutarate permease gene to reduce a export of α-ketoglutaric acid is known (WO01/005959).

As a method of enhancing an L-amino acid export, a method of enhancing lysE (a gene for basic L-amino acid exporter; J. Mol. Microbiol. Biotechnol., 1999 November; 1(2):327-36) in a strain of Corynebacterium bacterium is known for producing L-lysine (WO97/23597) or L-arginine (US Patent Publication 2003-0113899). A method of enhancing the expression of rhtA, B, C gene (JP 2000-189177A) and yfiK, yahN gene (EP 1016710A), which have been suggested to be involved in export of L-amino acids, in cells of Escherichia bacterium are also known.

As a gene for export of basic L-amino acids, the aforementioned lysE gene is known. However, when a lysE gene is amplified in a methanol-assimilating bacterium such as Methylophilus bacterium, and the resulting strain is used for production of L-lysine or L-arginine, a wild-type lysE gene derived from a Coryneform bacterium is lethal for the Methylophilus bacterium, and thus it is necessary to introduce a mutant lysE gene (EP 1266966A) that allows growth of the host microorganism. Therefore, the lysE gene cannot always function in export of L-lysine or L-arginine when it is introduced into heterogeneous microorganisms. Therefore, it is desirable to obtain a gene for L-amino acid exporter and production that exhibits an ability to export sufficient amounts of L-amino acids, including L-lysine and L-arginine, in a variety of heterogeneous host microorganisms.

The ybjE gene is located on the genome of Escherichia coli and has been predicted to encode a putative surface protein (Science, 277 (5331):1453-74, 1997). However, cloning of the gene and analysis thereof through expression in bacterial cells has not been reported, and thus its physiological function has remained unknown.

SUMMARY OF THE INVENTION

An object of the present invention is to provide a bacterial strain that can efficiently produce an L-amino acid. Another object of the present invention is to provide a method for efficiently producing an L-amino acid using such a strain.

The inventors of the present invention assiduously studied in order to achieve the aforementioned objects, and as a result, obtained the ybjE gene, a novel gene for L-amino acid exporter, based on a resistance to high concentrations of L-lysine. Furthermore, they also found that L-amino acids, including basic L-amino acids such as L-lysine, L-arginine, L-ornithine, and L-histidine; aliphatic L-amino acids such as L-isoleucine; hydroxyl L-amino acids such as L-threonine; circular L-amino acids such as L-proline; aromatic L-amino acids such as L-phenylalanine; sulfur-containing L-amino acids such as L-cysteine; and acidic L-amino acids such as L-glutamic acid, can be efficiently produced using a microorganism in which expression of the ybjE gene is enhanced.

It is an object of the present invention to provide a microorganism having an L-amino acid-producing ability, wherein said microorganism is modified so that expression of a ybjE gene is enhanced.

It is a further object of the present invention to provide the microorganism as stated above, wherein the expression of said ybjE gene is enhanced by increasing a copy number of said ybjE gene, or by modifying an expression regulatory sequence of said ybjE gene.

It is a further object of the present invention to provide the microorganism as stated above, wherein the amino acid sequence of a protein encoded by said ybjE gene is selected from the group consisting of SEQ ID NO: 2, 9, and 10, wherein said protein has an L-amino acid-export ability.

It is a further object of the present invention to provide the microorganism as stated above, wherein said ybjE gene is selected from the group consisting of:
(a) a DNA comprising a nucleotide sequence of SEQ ID NO: 1; and
(b) a DNA hybridizable under stringent conditions with a nucleotide sequence of SEQ ID NO: 1 or a probe that can be prepared from the nucleotide sequence of SEQ ID NO: 1, and wherein said DNA encodes a protein having an L-amino acid-export ability.

It is a further object of the present invention to provide the microorganism as stated above, wherein said ybjE gene is selected from the group consisting of:
(a) a DNA having a nucleotide sequence of nucleotide numbers 49 to 948 in SEQ ID NO: 1; and
(b) a DNA hybridizable under stringent conditions with a nucleotide sequence of nucleotide numbers 49 to 948 in SEQ ID NO: 1 or a probe that can be prepared from the nucleotide sequence of nucleotide numbers 49 to 948 in SEQ ID NO: 1, and wherein said DNA encodes a protein having an L-amino acid-export ability.

It is a further object of the present invention to provide the microorganism as stated above, wherein said L-amino acid-export ability of said microorganism is increased by said enhancing the expression of said ybjE gene.

It is a further object of the present invention to provide the microorganism stated above, wherein a resistance of the microorganism to an L-amino acid or L-amino acid analogue is increased by said enhancing expression of said ybjE gene.

It is a further object of the present invention to provide the microorganism as stated above, wherein said L-amino acid is selected from the group consisting of L-lysine, L-arginine, L-ornithine, L-histidine, L-isoleucine, L-threonine, L-proline, L-phenylalanine, L-cysteine, and L-glutamic acid.

It is a further object of the present invention to provide the microorganism as stated above, wherein said microorganism belongs to an Enterobacteriaceae family.

It is a further object of the present invention to provide the microorganism as stated above, wherein said microorganism belonging to Enterobacteriaceae family is a microorganism belonging to the genus *Escherichia*.

It is a further object of the present invention to provide the microorganism as stated above, wherein said microorganism is a *Coryneform* bacterium.

It is a further object of the present invention to provide the microorganism as stated above, wherein said microorganism is a methanol-assimilating microorganism.

It is a further object of the present invention to provide the microorganism as stated above, wherein said methanol-assimilating microorganism belongs to the genus *Methylophilus* or *Methylobacillus*.

It is a further object of the present invention to provide a method for producing an L-amino acid comprising culturing the microorganism as stated above in a medium to produce and cause accumulation of said L-amino acid, and collecting said L-amino acid from the medium or the microorganism.

It is a further object of the present invention to provide a method for producing an L-amino acid, comprising culturing the microorganism as stated above in a liquid medium containing methanol as a major carbon source to produce and cause accumulation of said L-amino acid, and collecting the L-amino acid from the medium or the microorganism.

It is a further object of the present invention to provide the method as stated above, wherein the L-amino acid is selected from the group consisting of L-lysine, L-arginine, L-ornithine, L-histidine, L-isoleucine, L-threonine, L-proline, L-phenylalanine, L-cysteine, and L-glutamic acid.

DETAILED DESCRIPTION OF THE PREFERRED EMBODIMENTS

Figure 1:
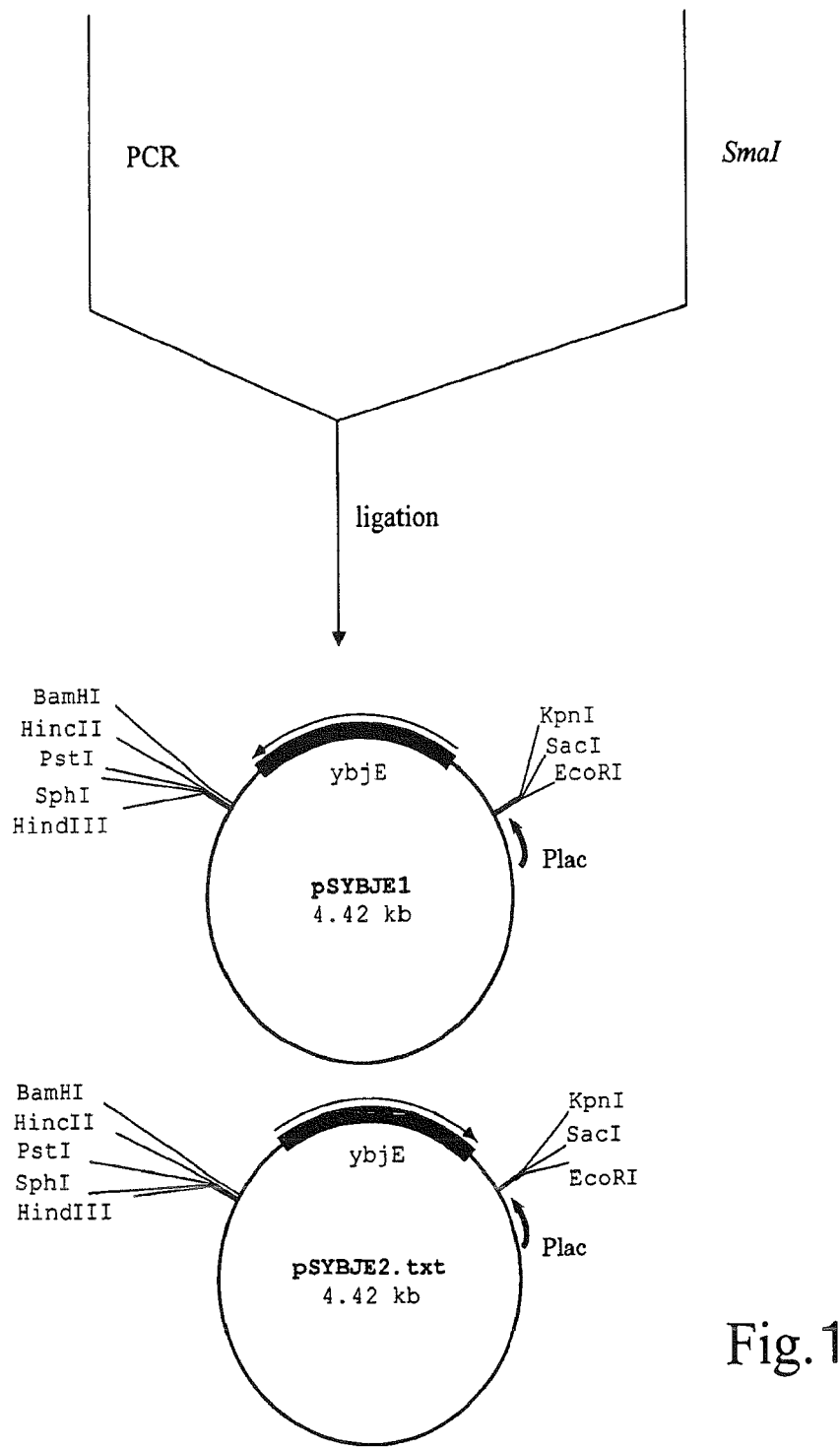
FIG. 1 shows a construction scheme of a plasmid for amplification of the ybjE gene in *Escherichia* bacteria.

Hereafter, the present invention will be explained in detail.
<1> Microorganism of the Present Invention
The microorganism of the present invention has an ability to produce an L-amino acid and has been modified so that expression of the ybjE gene is enhanced. The phrase "ability to produce an L-amino acid (L-amino acid-producing ability)" as used herein means an ability to cause accumulation of an L-amino acid in a medium or in the cells of the microorganism when the microorganism of the present invention is cultured in the medium. The microorganism of the present invention may have an ability to produce multiple kinds of L-amino acids. The microorganism having an L-amino acid-producing ability may be a microorganism originally having an L-amino acid-producing ability, or may be a microorganism obtained by modifying a parent strain of a microorganism as mentioned below using a mutagenesis technique or recombinant DNA technique so that the microorganism has an L-amino acid-producing ability. The microorganism of the present invention may also be a microorganism which has obtained an L-amino acid-producing ability by enhancing the ybjE gene expression.

L-amino acids to be produced in the present invention are not particularly limited, and include basic L-amino acids such as L-lysine, L-arginine, L-ornithine, L-histidine, and L-citrulline; aliphatic L-amino acids such as L-isoleucine, L-alanine, L-valine, L-leucine, and L-glycine; hydroxyl L-amino acids such as L-threonine and L-serine; circular L-amino acids such as L-proline; aromatic L-amino acids such as L-phenylalanine, L-tyrosine, and L-tryptophane; sulfur-containing L-amino acids such as L-cysteine, L-cystine, and L-methionine; and acidic L-amino acids and their amides such as L-glutamic acid, L-aspargic acid, L-glutamine, and L-asparagine. The microorganism of the present invention may have an ability to produce two or more kinds of these L-amino acids.

<Imparting L-Amino Acid-Producing Ability>

Examples of microorganisms having an L-amino acid-producing ability to be used in the present invention will be described below. However, the microorganisms are not limited to the examples, but include any microorganism having an L-amino acid-producing ability.

As a parent strain of the microorganism of the present invention, Enterobacteriaceae family such as *Escherichia* bacteria, *Pantoea* bacteria, or *Coryneform* bacteria, and so forth may be used. In addition, methanol-assimilating bacteria, such as *Methylophilus* bacteria and *Methylobacillus* bacteria, which can produce L-amino acids from methanol, may also be used. Furthermore, examples of parent strains include Enterobacteriaceae family belonging to γ-proteobacteria including bacteria belonging to the genus *Escherichia, Pantoea, Enterobacter, Klebsiella, Serratia, Erwinia, Salmonella* and *Morganella*, and other bacteria including *Alicyclobacillus* bacteria and *Bacillus* bacteria, and yeasts including those belonging to the genus *Saccharomyces, Candida*, or the like. These parent strains may inherently possesses the ybjE gene, or may not inherently possess ybjE gene and exhibit improved L-amino acid-export ability when the ybjE gene is introduced.

*Escherichia* bacteria reported in Neidhardt et al. (Neidhardt, F. C. et al., *Escherichia coli* and *Salmonella Typhimurium*, American Society for Microbiology, Washington D.C., 1208, Table 1), such as *Escherichia coli*, can be utilized. Examples of wild-type strains of *Escherichia coli* include, but are not limited to, the K12 strain and derivatives thereof, *Escherichia coli* MG1655 strain (ATCC No. 47076), and W3110 strain (ATCC No. 27325). These strains are available from the American Type Culture Collection (ATCC, Address: P.O. Box 1549, Manassas, Va. 20108, United States of America).

Examples of *Enterobacter* bacteria include *Enterobacter agglomerans, Enterobacter aerogenes*, and so forth. Examples of *Pantoea* bacteria include *Pantoea ananatis* and so forth. Although some bacteria originally classified as *Enterobacter aerogenes* may be now classified as *Pantoea agglomerans, Pantoea ananatis* or *Pantoea stewartii* based on 16S rRNA analysis, the microorganism belonging to the Enterobacteriaceae family used in the present invention may be either *Enterobacter* bacteria or *Pantoea* bacteria. Specific examples of *Pantoea ananatis* include *Pantoea ananatis* AJ13355 (FERM BP-6614), *Pantoea ananatis* AJ13356 (FERM BP-6615), *Pantoea ananatis* AJ13601 (FERM BP-7207), and derivatives thereof. These strains were originally identified and deposited as *Enterobacter agglomerans*, and are now classified as *Pantoea ananatis*.

Examples of *Methylophilus* bacteria include, but are not limited to, *Methylophilus methylotrophus*, and typical examples of *Methylophilus methylotrophus* include the AS1 strain (NCIMB10515) and so forth. The *Methylophilus methylotrophus* AS1 strain (NCIMB 10515) is available from the National Collections of Industrial and Marine Bacteria (Address: NCIMB Lts., Torry Research Station, 135, Abbey Road, Aberdeen AB9 8DG, United Kingdom).

Examples of *Methylobacillus* bacteria include, but are not limited to, *Methylobacillus glycogenes, Methylobacillus flagellatum*, and so forth. Examples of *Methylobacillus glycogenes* include the T-11 strain (NCIMB 11375), ATCC 21276 strain, ATCC 21371 strain, ATR80 strain (Appl. Microbiol. Biotechnol., vol. 42, pp. 67-72 (1994)), A513 strain (Appl. Microbiol. Biotechnol., vol. 42, pp. 67-72 (1994)), and so forth. The *Methylobacillus glycogenes* NCIMB 11375 strain is available from the National Collections of Industrial and Marine Bacteria (Address: NCIMB Lts., Torry Research Station 135, Abbey Road, Aberdeen AB9 8DG, United Kingdom). Examples of *Methylobacillus flagellatum* include the KT strain (Arch. Microbiol., vol. 149, pp. 441-446 (1988)) and so forth.

The *Coryneform* bacteria are a group of microorganisms defined in Bergey's Manual of Determinative Bacteriology, 8th Ed., p. 599 (1974), and may be used in the present invention. These microorganisms are classified into aerobic, Gram-positive, and nonacid-fast bacilli incapable of sporulating. The *Coryneform* bacteria also include those bacteria having been hitherto classified into the genus *Brevibacterium*, but are currently united into the genus *Corynebacterium* (Int. J. Syst. Bacteriol., 41, 255 (1991)), as well as bacteria belonging to the genus *Brevibacterium* or *Microbacterium* which are closely related to the genus *Corynebacterium*.

Examples of such *Coryneform* bacteria are listed below.
*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Corynebacterium ammoniagens*
*Brevibacterium album*
*Brevibacterium cerinum*
*Microbacterium ammoniaphilum*

Specifically, the following strains can be exemplified.
*Corynebacterium acetoacidophilum* ATCC13870
*Corynebacterium acetoglutamicum* ATCC15806
*Corynebacterium alkanolyticum* ATCC21511
*Corynebacterium callunae* ATCC15991
*Corynebacterium glutamicum* ATCC13020, ATCC13032, ATCC13060
*Corynebacterium lilium* ATCC15990
*Corynebacterium melassecola* ATCC17965
*Corynebacterium efficiens* AJ12340 (FERM BP-1539)

*Corynebacterium herculis* ATCC13868
*Brevibacterium divaricatum* ATCC14020
*Brevibacterium flavum* ATCC13826, ATCC14067, AJ12418 (FERM BP-2205)
*Brevibacterium immariophilum* ATCC14068
*Brevibacterium lactofermentum* ATCC13869 (*Corynebacterium glutamicum* ATCC13869)
*Brevibacterium roseum* ATCC13825
*Brevibacterium saccharolyticum* ATCC14066
*Brevibacterium thiogenitalis* ATCC19240
*Corynebacterium ammoniagenes* ATCC6871, ATCC6872
*Brevibacterium album* ATCC15111
*Brevibacterium cerinum* ATCC15112
*Microbacterium ammoniaphilum* ATCC15354

These strains can be obtained, for example, from the American Type Culture Collection. Each strain is given a unique registration number which is listed in the catalogue of the American Type Culture Collection. Strains can be ordered using this registration number. Furthermore, the AJ12340 strain was deposited on Oct. 27, 1987 at the National Institute of Bioscience and Human-Technology, Agency of Industrial Science and Technology, Ministry of International Trade and Industry (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-5466)) as an international deposit under the provisions of the Budapest Treaty, and received an accession number of FERM BP-1539. The AJ12418 strain was deposited on Jan. 5, 1989 at the National Institute of Advanced Industrial Science and Technology, International Patent Organism Depositary as an international deposit under the provisions of the Budapest Treaty and received an accession number of FERM BP-2205.

Hereinafter, methods for imparting an L-amino acid-producing ability to a parent strain as mentioned above will be explained.

In order to impart L-amino acid-producing ability, methods conventionally used for breeding an L-amino acid-producing bacterium belonging to the genus *Escherichia* or *Coryneform* bacterium and so forth can be used. For example, methods for obtaining an auxotrophic mutant strain, analogue-resistant strain, or metabolic regulation mutant strain having L-amino acid-producing ability, and methods for creating a recombinant strain having enhanced activity of an L-amino acid-biosynthetic enzyme can be used ("Amino Acid Fermentation", the Japan Scientific Societies Press [Gakkai Shuppan Center], 1st Edition, published on May 30, 1986, pp. 77-100). When breeding L-amino acid-producing bacteria using these methods, one or more properties, including auxotrophy, analogue resistance, and metabolic regulation mutation, may be imparted.

When a recombinant strain is created, the activity of single or multiple L-amino acid-biosynthetic enzymes may be enhanced. Furthermore, methods imparting properties of auxotrophy, analogue resistance, and metabolic regulation mutation may be combined with methods enhancing an activity of L-amino acid-biosynthetic enzyme.

An auxotrophic mutant strain, L-amino acid analogue-resistant strain, or metabolic regulation-mutated strain having an L-amino acid-producing ability can be obtained by subjecting a parent or wild-type strain to a typical mutagenesis treatment such as X-ray or ultraviolet ray irradiation, treatment with a mutagenesis agent such as N-methyl-N'-nitro-N-nitrosoguanidine (NTG). Then, an auxotrophic strain, analogue-resistant strain or metabolic regulation mutant strain which has an L-amino acid-producing ability may be selected from the mutated strains.

Examples of L-lysine analogues include oxalysine, lysine hydroxamate, S-(2-aminoethyl)-L-cysteine (AEC), γ-methyllysine, α-chlorocaprolactam, norleucine, and so forth. Examples of L-arginine analogues include arginine hydroxamate, homoarginine, D-arginine, canavanine, arginine hydroxamate.

Specific examples of L-lysine analogue-resistant strains or metabolic regulation-mutated strains having an L-lysine-producing ability include the *Escherichia coli* AJ11442 strain (FERM BP-1543, NRRL B-12185, JP 56-18596A and U.S. Pat. No. 4,346,170), *Escherichia coli* VL611 strain (JP 2000-189180A), and so forth. Furthermore, the WC1-96 strain (WO96/17930) may also be used as an L-lysine-producing *Escherichia coli*. The WC1-96 strain was originally bred by imparting AEC (S-(2-aminoethyl)cysteine)-resistance to the W3110 strain, which is derived from *Escherichia coli* K-12. The WC1-96 strain was designated as *Escherichia coli* AJ13069 strain, and was deposited at the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Dec. 6, 1994 and received an accession number of FERM P-14690. Then, the deposit was converted to an international deposit under the provisions of the Budapest Treaty on Sep. 29, 1995, and received an accession number of FERM BP-5252.

Examples of *Coryneform* bacteria having L-lysine-producing ability include S-(2-aminoethyl)cysteine (hereinafter "AEC")-resistant mutant strains including *Brevibacterium lactofermentum* AJ11082 (NRRL B-11470) (described in JP56-1914B, JP56-1915B, JP57-14157B, JP57-14158B, JP57-30474B, JP58-10075B, JP59-4993B, JP61-35840B, JP62-24074B, JP62-36673B, JP5-11958B, JP7-112437B and JP7-112438B), mutant strains auxotrophic for an amino acid such as L-homoserine (JP48-28078B and JP56-6499B), mutant strains resistant to AEC and auxtrophic for an amino acid such as L-leucine, L-homoserine, L-proline, L-serine, L-arginine, L-alanine, and L-valine (U.S. Pat. Nos. 3,708,395 and 3,825,472), L-lysine-producing mutant strains resistant to DL-α-amino-ε-Caprolactam, α-amino-lauryllactam, aspartic acid analogue, sulfa drug, quinoid, and N-lauroylleucine, L-lysine-producing mutant strains resistant to oxaloacetate decarboxylase inhibitor or a respiratory tract enzyme inhibitor (JP50-53588A, JP50-31093A, JP52-102498A, JP53-9394A, JP53-86089A, JP55-9783A, JP55-9759A, JP56-32995A, JP56-39778A, JP53-43591B and JP53-1833B), L-lysine-producing mutant strains auxotrophic for inositol or acetic acid (JP55-9784A and JP56-8692A), L-lysine-producing mutant strains that are susceptible to fluoropyruvic acid or a temperature of 34° C. or higher (JP55-9783A and JP53-86090A), L-lysine-producing mutant strains of *Brevibacterium* or *Corynebacterium* bacteria resistant to ethylene glycol (U.S. Pat. No. 4,411,997), and so forth.

An L-amino acid-producing ability may also be imparted by enhancing expression of a gene encoding for an L-amino acid biosynthetic enzyme.

For example, an L-lysine-producing ability can be imparted by enhancing expression of a gene encoding dihydrodipicolinate synthase and a gene encoding aspartokinase. That is, a recombinant DNA is prepared by ligating a gene fragment encoding dihydrodipicolinate synthase and a gene fragment encoding aspartokinase into a vector, preferably a multi-copy vector, which is operable in the host microorganism used for L-lysine production. As a result of the transformation, copy numbers of the gene encoding dihydrodipicolinate synthase and the gene encoding aspartokinase increase in the host cell, and thereby activities of these enzymes are enhanced. Hereinafter, dihydrodipicolinate synthase, aspartokinase, and aspartokinase III are also referred to by their respective abbreviations' DDPS, AK and AKIII.

The genes encoding DDPS and AK are not particularly limited, so long as they encode proteins having DDPS or AK activity, respectively. Examples of such genes include the genes of *Escherichia coli, Methylophilus methylotrophus, Corynebacterium glutamicum,* and so forth. Since the nucleotide sequences are known for a DDPS gene (dapA, Richaud, F. et al., J. Bacteriol., 297 (1986)) and an AKIII gene (lysC, Cassan, M., Parsot, C., Cohen, G. N. and Patte, J. C., J. Biol. Chem., 261, 1052 (1986)), these genes can be obtained by PCR using primers designed based on their nucleotide sequences from chromosomal DNA of a microorganism such as *E. coli* K-12 strain. Hereinafter, a gene encoding DDPS and a gene encoding AK will be exemplified by dapA and lysC derived from *E. coli*, but genes encoding DDPS and genes encoding AK are not limited to dapA and lysC.

It is known that wild-type DDPS derived from *Escherichia coli* is subject to feedback inhibition by L-lysine, and that wild-type AKIII derived from *Escherichia coli* is subject to suppression and feedback inhibition by L-lysine. Therefore, when dapA and lysC are used, it is preferable to use mutant genes encoding DDPS and AK that are resistant to the feedback inhibition by L-lysine. Hereinafter, DDPS having a mutation that releases from the feedback inhibition by L-lysine may also be referred to as "mutant DDPS", and a DNA encoding the mutant DDPS may also be referred to as "mutant dapA" or "dapA*". AKIII derived from *Escherichia coli* having a mutation that eliminates the feedback inhibition by L-lysine may also be referred to as "mutant AKIII", and a DNA encoding the mutant AKIII may also be referred to as "mutant lysC". DDPS derived from *Corynebacterium* bacteria is originally resistant to feedback inhibition by L-lysine, and therefore DDPS and AK used for the present invention do not necessarily need to be mutated.

Examples of the DNA encoding mutant DDPS that is resistant to feedback inhibition by L-lysine include a DNA encoding DDPS having an amino acid sequence which includes substituting the 118-histidine residue with tyrosine. (U.S. Pat. Nos. 5,661,012 and 6,040,160). Furthermore, examples of the DNA encoding mutant AKIII that is resistant to feedback inhibition by L-lysine include a DNA encoding AKIII having the amino acid sequence which includes substituting the 352-threonine residue with isoleucine. (U.S. Pat. Nos. 5,661,012 and 6,040,160). A mutant DNA can be obtained by a site-directed mutagenesis technique using PCR or the like.

The plasmid used for gene cloning may be any plasmid so long as it can replicate in microorganisms, and specific examples thereof include pBR322, pTWV228 (Takara Bio), pMW119 (Nippon Gene), pUC19, and so forth.

A vector operable in a host microorganism used for transformation is a plasmid that is autonomously replicable in cells of each microorganism. Specific examples of vectors for *Escherichia coli* include pSTV29 (Takara Bio), RSF1010 (Gene, vol. 75 (2), pp. 271-288, 1989), pUC19, pBR322, pMW119, and so forth. Phage DNA vectors may also be used. The vector for *Methylophilus* bacteria, for example, is a plasmid that is autonomously replicable in cells of *Methylophilus* bacteria. Specific examples of vectors for *Methylophilus* bacteria include RSF1010 and derivatives thereof, such as pAYC32 (Chistorerdov, A. Y., Tsygankov, Y. D. Plasmid, 16, 161-167 (1986)), pMFY42 (Gene, 44, 53 (1990)), pRP301, and pTB70 (Nature, 287, 396, (1980)). Examples of a vector operable in *Coryneform* bacteria include pAM330 (JP58-67699A), pHM1519 (JP58-77895A), and pSFK6 (JP2000-262288A). Moreover, vectors obtained by excising a DNA fragment which enables a plasmid to autonomously replicate in a *Coryneform* bacterium and inserting the fragment into vectors for *Escherichia coli* can be used as a so-called shuttle vector which is autonomously replicable both in *Escherichia coli* and *Coryneform* bacteria.

To prepare a recombinant DNA via ligation of dapA and lysC with any of the above-cited vectors, restriction enzymes can be used to digest both the DNA fragment containing dapA and lysC and the vector. Ligation is usually performed using a ligase such as T4 DNA ligase. dapA and lysC may be incorporated into separate vectors or into a single vector. Methods which can be used for restriction enzyme digestion, ligation of DNA, preparation of chromosomal DNA, PCR, preparation of plasmid DNA, transformation, design of oligonucleotide primers, and so forth, may be usual methods well known to those skilled in the art. Such methods are described in Sambrook, J., Fritsch, E. F., and Maniatis, T., "Molecular Cloning A Laboratory Manual, Second Edition", Cold Spring Harbor Laboratory Press (1989) and so forth. In order to introduce a recombinant DNA prepared as described above into a microorganism, any method can be used so long as sufficient transformation efficiency is attained. For example, electroporation can be applied (Canadian Journal of Microbiology, 43, 197 (1997)).

The broad host spectrum plasmid RSFD80 may be used (U.S. Pat. No. 6,040,160) as the plasmid containing a mutant dapA encoding a mutant DDPS and mutant lysC encoding a mutant AKIII *Escherichia coli* JM109 strain transformed with RSFD80 was designated AJ12396 (U.S. Pat. No. 6,040, 160), and this strain was deposited at the independent administrative agency, National Institute of Advanced Industrial Science and Technology, International Patent Organism Depositary on Oct. 28, 1993 and received an accession number of FERM P-13936. Then, the deposit was converted to an international deposit under the provisions of the Budapest Treaty on Nov. 1, 1994, and received an accession number of FERM BP-4859. RSFD80 can be obtained from the AJ12396 strain by a known method. Expression of the DDPS gene and AK gene can also be enhanced by integrating multiple copies of dapA and lysC into a chromosomal DNA of a microorganism. In order to introduce multiple copies of dapA and lysC into a chromosomal DNA of a microorganism, homologous recombination can be performed by targeting a sequence that is present on the chromosomal DNA in multiple copies. A repetitive DNA or an inverted repeat present at the end of a transposable element can be used as a sequence present on a chromosomal DNA in multiple copies. Alternatively, as disclosed in JP2-109985A, multiple copies of dapA and/or lysC can be introduced into a chromosomal DNA by using a transposon. In both of the methods, activities of DDPS and AK are enhanced as a result of the increased copy numbers of dapA and lysC in the transformed strains.

Besides the above-mentioned gene amplification methods, expression of the DDPS gene and AK gene can also be enhanced by replacing an expression regulatory sequence, such as promoters of dapA and lysC, with stronger ones (JP1-215280A). Examples of such strong promoters include lac promoter, trp promoter, trc promoter, tac promoter, $P_R$ promoter and $P_L$ promoter of lambda phage, tet promoter, amyE promoter, spac promoter, and so forth. Insertion of these promoters in the place of native promoters enhances expression of dapA and lysC, resulting in enhancement of DDPS and AK activity. Enhancing expression regulatory sequences may be combined with amplifying copy numbers of dapA and lysC.

An L-lysine-producing ability may also be imparted by enhancing the expression of a gene encoding an L-lysine-biosynthetic enzyme other than DDPS and AK. Examples of such enzymes include enzymes of diaminopimelate-synthetic pathway such as dihydrodipicolinate reductase, diaminopimelate decarboxylase, diaminopimelate dehydrogenase (WO96/40934), phosphoenolpyruvate carboxylase (JP60-87788A), aspartate aminotransferase (JP6-102028B), diaminopimelate epimerase (JP2003-135066A), and aspartate semialdehyde dehydrogenase (WO00/61723). Further examples of such enzymes include amino adipate pathway enzymes such as homoaconitate hydratase (JP2000-157276A) and so forth. Enhancing gene expression of these enzymes may be combined with enhancing expression of the DDPS and AK genes.

Furthermore, a microorganism having an L-lysine-producing ability can also be obtained by reducing or eliminating an intracellular activity of an enzyme that catalyzes a reaction for synthesizing a compound other than L-lysine, and branching from the L-lysine biosynthetic pathway. Examples of such enzymes include homoserine dehydrogenase and lysine decarboxylase. Strains in which activities of these enzymes are reduced or eliminated are described in WO95/23864 and WO96/17930.

Examples of methods of reducing or eliminating the intracellular activity of an enzyme include mutating or deleting a gene encoding the enzyme in cells of a microorganism so that intracellular activity is reduced or eliminated as compared to a non-mutated strain. Examples of methods of mutating or deleting a gene include modification of expression regulatory sequences such as promoters and Shine-Dalgarno (SD) sequences, introduction of mis-sense mutations, non-sense mutations, or frame-shift mutations into an open reading frame, and deletion of a portion of the gene (J Biol. Chem. 1997 272(13):8611-7). A mutated gene can be introduced into a microorganism by using a homologous recombination technique in which a wild-type gene on a chromosome is replaced with the mutated gene, or by using a transposon or IS factor. Homologous recombination techniques include methods using linear DNA, a temperature-sensitive plasmid, and non-replicable plasmid. These methods are described in Proc Natl Acad Sci USA. 2000 Jun. 6; 97(12):6640-5., U.S. Pat. No. 6,303,383, JP05-007491A, and the like.

The methods of enhancing and reducing L-lysine biosynthesis enzyme activity are applicable to imparting another L-amino acid-producing ability. Specific examples of *Escherichia coli* which have an ability to produce L-arginine include mutant strains resistant to α-methylmethionine, p-fluorophenylalanine, D-arginine, arginine hydroxamate, S-(2-aminoethyl)cysteine, α-methylserine, β-2-thienylalanine, or sulfaguanidine (JP No. 56-106598A), and so forth. In addition, the *Escherichia coli* 237 strain, which is an L-arginine-producing bacterium having a mutation which imparts resistance to feedback inhibition by L-arginine and exhibiting high N-acetylglutamate synthase activity (Russian Patent Application No. 2000117677), can also be used. This strain was deposited at the Russian National Collection of Industrial Microorganisms (VKPM), GNII Genetika with a number of VKPM B-7925 on Apr. 10, 2000, and converted to an international deposit under the provisions of the Budapest Treaty on May 18, 2001. The *Escherichia coli* 382 strain, which is derived from 237 the strain and has an enhanced acetate-assimilating ability, can also be used (JP2002-017342A). The *Escherichia coli* 382 strain was deposited at the Russian National Collection of Industrial Microorganisms (VKPM) with a number of VKPM B-7926 on Apr. 10, 2000.

Examples of *Coryneform* bacteria having an L-arginine-producing ability include strains of *Coryneform* bacterium which are not only resistant to 2-thiazolealanine but are also auxotrophic for L-histidine, L-proline, L-threonine, L-isoleucine, L-methionine, or L-tryptophan (JP54-44096A), a strain of *Coryneform* bacterium resistant to ketomalonic acid, fluoromalonic acid, or monofluoroacetic acid (JP57-18989A), a strain of *Coryneform* bacterium resistant to argininol (JP62-24075A), a strain of *Coryneform* bacterium resistant to X-guanidine (X represents a derivative of a fatty acid or an aliphatic chain, JP2-186995A), a strain of *Coryneform* bacterium resistant to arginine hydroxamate and 6-azauracil (JP57-150381A), a strain of *Coryneform* bacterium which is deficient in ArgR (a repressor protein of the arginine biosynthetic enzymes) (JP2002-51790A), and so forth.

Activities of biosynthesis enzymes for L-arginine, L-histidine, L-ornithine, and other L-amino acids can be enhanced by methods similar to the aforementioned methods for L-lysine-biosynthetic enzymes.

Examples of L-arginine-biosynthetic enzymes include one or more kinds of enzymes selected from N-acetylglutamate synthase (argA), N-acetylglutamyl phosphate reductase (argC), ornithine acetyltransferase (argJ), N-acetylglutamate kinase (argB), acetylornithine transaminase (argD), acetylornithine deacetylase (argE) ornithine carbamoyltransferase (argF), argininosuccinate synthase (argG), argininosuccinate lyase (argH), and carbamoyl-phosphate synthase (carAB). The names of the genes encoding these enzymes are given in parentheses after the names of the enzymes, respectively. Examples of the strains in which activities of these enzymes are enhanced include, for example, the strains described in JP2000-287693A, JP2000-197490A, JP07-028749B, and so forth.

An L-arginine-producing ability may also be imparted by enhancing expression of a gene encoding glutamate dehydrogenase (EP1057893A) or enhancing glutamate synthetase activity (US2005-00142236).

It is known that L-arginine-biosynthetic enzymes are suppressed by L-arginine, and therefore L-arginine-producing ability may also be efficiently enhanced by deleting an arginine repressor or introducing a mutation into N-acetylglutamine synthase (EP1154020A and EP1170361A) which confers resistance to feedback inhibition.

Furthermore, *Bacillus* bacteria resistant to a histidine analogue or a tryptophan analogue (JP52-114092A), *Bacillus* bacteria auxotrophic for at least one of L-methionine, L-histidine, L-threonine, L-proline, L-isoleucine, L-lysine, adenine, guanine, and uracil (or uracil precursor) (JP52-99289A), *Bacillus* bacteria resistant to arginine hydroxamate (JP51-6754B), *Serratia marcescens* auxotrophic for succinic acid or resistant to a nucleotide analogue (JP58-9692A), *Serratia marcescens* which is deficient in an ability to metabolize arginine, resistant to an arginine antagonist and canavanine, and auxotorophic for lysine (JP52-8729A), *Saccharomyces cerevisiae* resistant to arginine, arginine hydroxamate, homoarginine, D-arginine, canavanine, arginine hydroxamate and 6-azauracil (JP53-143288A), *Candida tropicalis* resistant to canavanine (JP53-3586A), and so forth can also be used as L-arginine-producing strains.

Examples of the L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore an L-histidine-producing ability can also be efficiently enhanced by introducing a mutation conferring resistance to the feedback inhibition into ATP phosphoribosyltransferase (hisG) (Russian Patent Nos. 2003677 and 2119536).

Specific examples of microorganisms which have an L-histidine-producing ability include *E. coli* strains FERM-P5038 and 5048 which have been introduced with a vector carrying a DNA encoding an L-histidine-bio synthetic enzyme (JP56-005099A), strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

The L-ornithine biosynthetic pathway includes several enzymes in common with the L-arginine biosynthetic pathway. Examples of L-ornithine-bio synthetic enzymes include N-acetylglutamate synthase (argA), N-acetylglutamyl phosphate reductase (argC), ornithine acetyltransferase (argJ), N-acetylglutamate kinase (argB), acetylornithine transaminase (argD), acetylornithine deacetylase (argE), and so forth.

Examples of bacteria having an ability to produce L-ornithine include *Coryneform* bacteria and *Arthrobacter* bacteria which have been introduced with an L-citrulline- or L-arginine-auxotrophic mutation (JP02-283290A), *Coryneform* bacterium AJ11589 strain resistant to a vitamin P-like active substance (FERM-P5644, JP57-016696A), and so forth.

Examples of microorganisms having an L-threonine-producing ability include a 6-dimethylaminopurine-resistant mutant which has an L-threonine-producing ability (JP5-304969A), a strain in which a gene for a threonine biosynthetic enzyme having a mutation for enhancing the enzymatic activity is amplified with a plasmid (JP1-29559B, JP05-227977A), a strain in which the threonine operon is amplified with a plasmid (JP2-109985A), a strain in which a gene encoding pyruvate carboxylase and a gene encoding nicotinamide nucleotide transhydrogenase are amplified (JP2002-51787A), and so forth.

The *Escherichia coli* VKPM B-3996 strain (U.S. Pat. No. 5,175,107) may also be used as an L-threonine-producing strain. VKPM B-3996 was deposited at the Russian National Collection of Industrial Microorganisms (VKPM), GNII Genetika with a registration number of VKPM B-3996 on Nov. 19, 1987. The VKPM B-3996 strain harbors plasmid pVIC40 (International Patent Publication WO90/04636), which is obtained by inserting a threonine operon (thrABC) into plasmid pAYC32 having a streptomycin resistance marker gene (Chistorerdov, A. Y., Tsygankov, Y. D., Plasmid, 1986, 16, 161-167). Aspartokinase 1-homoserine dehydrogenase I encoded by a mutant thrA gene contained in pVIC40 is released from feedback inhibition by L-threonine.

The *Escherichia coli* VKPM B-5318 strain (EP 0593792B) may also be used as an L-threonine-producing strain. VKPM B-5318 was deposited at the Russian National Collection of Industrial Microorganisms (VKPM), GNII Genetika (VKPM GNII Genetika Address: Dorozhny proezd 1, Moscow 113545, Russia) with a registration number of VKPM B-5318 on May 3, 1990. The VKPM B-5318 strain is autotroph to L-isoleucine, and the threonine operon encoding the threonine biosynthesis enzyme is located downstream of the C1 temperature-sensitive repressor, PR-promoter, and N-terminal end of the Cro protein derived from λphage. Moreover, the strain harbors plasmid DNA constructed so that the expression of threonine biosynthesis gene is regulated by a promoter and repressor derived from λphage.

Furthermore, The *Escherichia coli* MG442 strain (U.S. Pat. No. 4,278,765) may also be used as an L-threonine-producing strain. The MG442 strain was deposited at the Russian National Collection of Industrial Microorganisms (VKPM) as CMIMB-1628.

The bacteria having an ability to produce L-threonine may be obtained by enhancing the activity of an L-threonine biosynthetic enzyme. Examples of genes encoding L-threonine biosynthetic enzymes include an aspartokinase III gene, an aspartate semialdehyde dehydrogenase gene, and so forth. The activity of an L-threonine biosynthetic enzyme may be enhanced in a bacterium in which a threonine-degrading enzyme activity is suppressed. Examples of a bacterium in which the activity of a threonine-degrading enzyme is suppressed include the TDH6 strain, which is deficient in threonine dehydrogenase activity (JP2001-346578A).

The bacteria having an ability to produce L-glutamic acid can also be obtained by enhancing the activity of an L-glutamic acid biosynthetic enzyme. Examples of L-glutamic acid biosynthetic enzymes include glutamate dehydrogenase, glutamine synthetase, glutamate synthase, isocitrate dehydrogenase, aconitate hydratase, citrate synthase, pyruvate carboxylase, phosphoenolpyruvate carboxylase, phosphoenolpyruvate synthase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase, and so forth.

Specifically, the bacteria having enhanced activity of these L-glutamic acid biosynthetic enzymes include strains of *Coryneform* bacterium disclosed in WO00/18935 and JP2000-232890A, and strains of Enterobacteriaceae family disclosed in JP2001-333769A, JP2000-106869A, JP2000-189169A, and JP2000-333769A.

The bacteria having an ability to produce L-glutamic acid can also be obtained by reducing or eliminating an activity of one or more enzymes which catalyze a reaction causing a branching from L-glutamic acid synthesis and producing a compound other than L-glutamic acid. Such enzymes include isocitrate lyase, α-ketoglutarate dehydrogenase, phosphate acetyltransferase, acetate kinase, acetohydroxy acid synthase, acetolactate synthase, formate acetyltransferase, lactate dehydrogenase, glutamate decarboxylase, 1-pyrophosphate dehydrogenase, and so forth.

Specifically, bacteria in which α-ketoglutarate dehydrogenase activity is reduced include *Brevibacterium lactofermentum* Δs strain disclosed in WO95/34672, *Brevibacterium lactofermentum* AJ12821 strain (FERM BP-4172) disclosed in JP6-237779A, *Escherichia coli* strains disclosed in JP5-244970A or JP7-203980A, and *Enterobacter agglomerans* strain disclosed in JP2001-333769A.

Examples of bacteria having an ability to produce L-cysteine include *Escherichia coli* strain in which cystathionin α-lyase activity is reduced (JP2003-169668A) and a strain of *Escherichia coli* (JP11-155571A) or *Coryneform* bacterium (JP2002-233384A) in which feedback inhibition of serine acetyltransferase L-cysteine is released.

Examples of *Escherichia* bacteria having an ability to produce L-proline include *Escherichia coli* 702 strain (VKPM B-8011) which is resistant to 3,4-dihydroxyproline and azathidin-2-carboxylate, and 702ilvA strain (VKPM B-8012) which is obtained by deleting the ilvA gene in 702 strain (JP2002-300874A).

Examples of *Escherichia* bacteria having an ability to produce L-phenylalanine include *Escherichia coli* AJ12739 strain (tyrA::Tn10, TyrR; VKPM B-8197) in which the tyrA and tyrR genes are deleted, *Escherichia coli* HW1089 strain in which a mutated pheA is introduced (U.S. Pat. No. 5,354,672) and *Escherichia coli* strain in which the yddG and yedA genes are amplified (WO 03/044192). Examples of *Coryneform* bacteria having an ability to produce L-phenylalanine include a strain which is auxotrophic for tyrosine and resistant to L-phenylalanyl-L-tyrosine (JP5-49489A).

Bacteria having an ability to produce L-tryptophan can be obtained by enhancing the activities of L-tryptophane biosynthetic enzymes including phosphoglycerate dehydrogenase and anthranilate synthase. These enzymes may be resistant to feedback inhibition by L-tryptophan or L-serine. For example, a bacterium having these feedback-resistant enzymes can be obtained by introducing plasmid pGH5, which contains a mutant serA gene encoding L-tryptophan-resistant phosphoglycerate dehydrogenase into *Escherichia coli* SV164 strain which harbors a gene encoding L-serine-resistant anthranilate synthase (WO94/08031).

Bacteria having an ability to produce L-tryptophan can also be obtained by enhancing the activities of L-tryptophan biosynthetic enzymes encoded by the tryptophan operon. Such enzymes include the L-tryptophan operon tryptophan synthase and anthranilate synthase. Examples of these bacteria include an *Escherichia coli* strain in which the tryptophan operon containing a gene encoding L-serine-resistant anthranilate synthase is introduced (JP57-71397A, JP62-244382A, and U.S. Pat. No. 4,371,614).

In addition, examples of bacteria having an ability to produce L-tryptophan include *Escherichia coli* AGX17(pGX44) [NRRL B-12263] strain auxotrophic for L-phenylalanine and L-tyrosine, and AGX6(pGX50)aroP [NRRL B-12264] strain harboring plasmid pGX50 containing the tryptophan operon (U.S. Pat. No. 4,371,614).

Examples of *Escherichia* bacteria having an ability to produce L-isoleucine include a mutant strain resistant to 6-dimethylaminopurine (JP5-304969A), a mutant strain resistant to L-isoleucinehydroxamate, thiaisoleucine, DL-ethionine or argininehydroxamate (JP5-130882A), and a recombinant strain in which a gene encoding threonine deaminase and acetohydroxylic acid synthase is amplified with a plasmid (JP2-458A, JP2-42988A and JP8-47397A).

Bacteria having an ability to produce L-valine can be obtained by enhancing activities of L-valine biosynthetic enzymes including those encoded by the ilvGMEDA operon, especially acetohydroxylate synthase encoded by the ilvG gene (JP02-748418B). These enzymes may be resistant to feedback inhibition by L-valine.

Bacteria having an ability to produce L-valine may be a bacterium in which expression of the acetolactate synthase III gene (ilvIH gene) is decreased.

Bacteria having an ability to produce L-valine may be resistant to amino acid analogues. Examples of such bacteria include a mutant strain which is auxotrophic for L-isoleucine and L-methionine and is resistant to D-ribose, purine nucleoside, or pyrimidine ribonucleoside (FERM P-1841, P-5556; JP53-025034A), and a mutant strain resistant to polyketonoid (FERM P-9325; JP04-045314B).

Examples of bacteria having an ability to produce L-alanine include a *Coryneform* bacterium strain which is deficient in $H^+$-ATPase activity (Appl Microbiol Biotechnol. 2001 November; 57(4):534-40) or a *Coryneform* bacterium strain in which aspartic acid β-decarboxylase gene is amplified (JP07-163383A).

<Enhancing Expression of the ybjE Gene>

The microorganism of the present invention can be obtained by modifying a microorganism having an L-amino acid-producing ability as described above so that expression of the ybjE gene is enhanced. Alternatively, expression of the ybjE gene may be enhanced first, followed by imparting an L-amino acid-producing ability.

The expression of the ybjE gene may be enhanced by either enhancing the expression of the endogenous ybjE gene via modification of an expression regulatory sequence such as a promoter, or by exogenously introducing the ybjE gene using a plasmid or the like. These techniques may be combined.

Enhancement of the ybjE gene expression can be confirmed by measuring the amount of RNA by ybjE gene expression in the bacterium of the present invention by northern hybridization or RT-PCR (Molecular cloning: Cold spring Harbor Laboratory Press, Cold spring Harbor (USA), 2001, and comparing it to that of a wild-type or non-modified strain. The expression of the ybjE gene in the microorganism of the present invention is enhanced more than that of a wild-type or non-modified strain, and preferably not less than 1.5-fold, more preferably not less than 2-fold, and most preferably not less than 3-fold of a wild-type or non-modified strain.

The ybjE gene may be from *Escherichia coli* or a homologue thereof. Examples of the ybjE gene from *Escherichia coli* include a gene encoding a protein having an amino acid sequence of the amino acid numbers 17 to 315 in SEQ ID NO: 2, preferably a gene having a nucleotide sequence of the nucleotide numbers 49 to 948 in SEQ ID NO: 1. Although the codon for Val at position 1 in the amino acid sequence of SEQ ID NO: 2 is gtg, it may be translated as Met, and the protein encoded by the ybjE gene may be a protein having an amino acid sequence of SEQ ID NO: 2 (1 to 315). In such a case, it is preferable to use DNA containing the nucleotide sequence of the nucleotide numbers 1 to 948 of SEQ ID NO: 1. However, it is clearly understood from the Examples that a microorganism usable for the production method of the present invention can be obtained by using a DNA containing the nucleotide sequence SEQ ID NO: 1 (49 to 948), regardless of which amino acid residue is the translation initiation codon.

A homologue of *Escherichia coli* ybjE gene refers to a gene which exhibits a high structural similarity to the *Escherichia coli* ybjE gene and enhances L-amino acid-export ability or L-amino acid-resistance, and L-amino acid-producing ability of the host microorganism. Examples of the ybjE gene homologue include a gene encoding a protein having an amino acid sequence of SEQ ID NO: 9 or NO: 10. The amino acid sequence of SEQ ID NO: 9 is a sequence which is conserved between *Escherichia coli* YbjE protein (SEQ ID NO: 2) and YbjE protein of *Salmonella typhimurium* LT2 strain. The amino acid sequence of SEQ ID NO: 10 is a sequence which is conserved between *Escherichia coli* YbjE protein and YbjE protein of *Yersinia pestis* CO92 YPO1361 strain.

The ybjE gene homologue may be a gene encoding a protein having a homology of 70% or more, preferably 80% or more, more preferably 90% or more, more preferably 95% or more, particularly preferably 98% or more, to the total amino acid sequence of SEQ ID NO: 2 or the amino acid sequence of amino acid numbers 17 to 315 in SEQ ID NO: 2, and having an L-amino acid-exportability. Examples of a ybjE gene homologue also include a protein having an amino acid sequence of SEQ ID NO: 9 or NO: 10 and having L-amino acid-export ability. The homology of amino acid sequence and DNA sequence can be determined using the algorithm BLAST (Pro. Natl. Acad. Sci. USA, 90, and 5873 (1993)) and FASTA (Methods Enzymol., 183, and 63 (1990)) by Karlin and Altschul. The programs BLASTN and BLASTX were developed based on the algorithm BLAST.

ybjE genes derived from a microorganism other than *E. coli* may be used and include a gene derived from *Shigella flexneri* 2a str. 2457T strain which has a sequence complementary to the nucleotide numbers 275793 to 276692 or 275793 to 276740 of GenBank Accession No. AE016980, a gene derived from *Salmonella typhimurium* LT2 strain which has a sequence complementary to the nucleotide numbers 97 to 996 of GenBank Accession No. AE008740, and a gene derived from *Yersinia pestis* CO92 strain which has a sequence complementary to the nucleotide numbers 197812 to 198708 of GenBank Accession No. AJ414147. Furthermore, a ybjE gene may be cloned from a *Coryneform* bacterium such as *Corynebacterium glutamicum* and *Brevibacterium lactofermentum*, *Pseudomonas* bacterium such as *Pseudomonas aeruginosa*, *Mycobacterium* bacterium such as *Mycobacterium tuberculosis* or the like, based on homology to the genes as exemplified above.

Furthermore, the ybjE gene of the present invention is not limited to a wild-type gene, but may be a mutant or artificially modified gene encoding a protein having an amino acid sequence of SEQ ID NO: 2, an amino acid sequence of amino acid numbers 17 to 315 in SEQ ID NO: 2, or an amino acid sequence of SEQ ID NO: 9 or 10. The encoded protein may include substitutions, deletions, or insertions, of one or several amino acid residues at one or more positions so long as the function of the encoded YbjE protein, namely, L-lysine-export ability, is maintained. Although the number of "several" amino acid residues referred to herein differs depending on positions in the three-dimensional structure or types of amino acid residues, it may be 2 to 20, preferably 2 to 10, more preferably 2 to 5. Substitution of amino acids is preferably a conserved substitution including substitution of ser or thr for ala, substitution of gln, his or lys for arg, substitution of glu, gln, lys, his or asp for asn, substitution of asn, glu or gln for asp, substitution of ser or ala for cys, substitution of asn, glu, lys, his, asp or arg for gln, substitution of gly, asn, gln, lys or asp for glu, substitution of pro for gly, substitution of asn, lys, gln, arg or tyr for his, substitution of leu, met, val or phe for ile, substitution of ile, met, val or phe for leu, substitution of asn, glu, gln, his or arg for lys, substitution of ile, leu, val or phe for met, substitution of trp, tyr, met, ile or leu for phe, substitution of thr or ala for ser, substitution of ser or ala for thr, substitution of phe or tyr for trp, substitution of his, phe or trp for tyr and substitution of met, ile or leu for val. The substitution, deletion, or insertion, of one or several nucleotides as described above also includes a naturally occurring mutation arising from individual differences, and differences in species of microorganisms that harbor the ybjE gene (mutant or variant).

Such genes can be obtained by modifying a nucleotide sequence shown in SEQ ID NO: 1 or a nucleotide sequence of nucleotide numbers 49 to 948 in SEQ ID NO: 1 by, for example, site-specific mutagenesis, so that one or more substitutions, deletions, or insertions are introduced at a specific site of the protein encoded by the gene.

Examples of the ybjE gene which has a mutation in the sequence of SEQ ID NO: 1 include the ybjE gene which has a sequence of SEQ ID NO: 1 in which the nucleotide (guanine) at the $3^{rd}$ position is replaced by adenine.

Furthermore, such genes can also be obtained by conventional mutagenesis treatments such as those mentioned below. Examples of mutagenesis treatments include treating a gene having a nucleotide sequence shown in SEQ ID NO: 1 or a nucleotide sequence of nucleotide numbers 49 to 948 in a SEQ ID NO: 1 in vitro with hydroxylamine, and treating a microorganism such as an *Escherichia* bacterium harboring the gene with ultraviolet ray irradiation or a mutagenesis agent used in a typical mutation treatments such as N-methyl-N'-nitro-N-nitrosoguanidine (NTG) or EMS (ethyl methanesulfonate). Whether these genes encode a protein having L-amino acid-export ability can be confirmed by, for example, expressing the genes in a suitable cell and determining if the amount of the L-amino acid exported into the medium is increased. Whether these genes confer L-amino acid resistance to a host microorganism can be confirmed by introducing the genes into a host microorganism, culturing the host in the presence of high concentrations of the L-amino acid, and comparing the growth of the microorganism to that of a control strain.

The ybjE gene also includes a DNA which is able to hybridize under stringent conditions with a nucleotide sequence of SEQ ID NO: 1, a nucleotide sequence of nucleotide numbers 49 to 948 in SEQ ID NO: 1, or a probe prepared from these sequences, and which encodes a protein having L-amino acid-export ability. "Stringent conditions" as used herein are conditions under which a so-called specific hybrid is formed, and a non-specific hybrid is not formed. It is difficult to clearly express this condition by using any numerical value. However, examples of stringent conditions include, those under which DNAs having high homology to each other, for example, DNAs having a homology of not less than 50%, hybridize to each other, and DNAs having homology lower than 50% do not hybridize to each other, and those under which DNAs hybridize to each other at a salt concentration with washing typical of Southern hybridization, i.e., washing once or preferably 2-3 times under 1×SSC, 0.1% SDS at 60° C., preferably 0.1×SSC, 0.1% SDS at 60° C., more preferably 0.1×SSC, 0.1% SDS at 68° C.

Expression of the ybjE gene can be enhanced by, for example, increasing the copy number of the ybjE gene in cells using genetic recombination techniques. For example, a recombinant DNA can be prepared by ligating a gene fragment containing the ybjE gene to a vector, preferably a multicopy vector, which can replicate in the host microorganism, and introducing the resulting vector into the host microorganism.

When the ybjE gene of *Escherichia coli* is used, it may be obtained by, for example, the PCR method (polymerase chain reaction, refer to White, T. J. et al., Trends Genet., 5, 185 (1989)) using primers designed based on a nucleotide sequence of SEQ ID NO: 1, for example, primers each having a sequence of SEQ ID NO: 5 or 6, and using chromosomal DNA of *Escherichia coli* as a template. The ybjE gene from other microorganisms may also be used, and can be obtained from their chromosomal DNA or chromosomal DNA library by PCR using oligonucleotide primers designed based on a sequence of their ybjE gene or a homologous sequence thereof or the YbjE protein from a different species of microorganisms, or by hybridization using an oligonucleotide probe prepared based on such sequence information. A chromosomal DNA can be prepared from a microorganism serving as a DNA donor by, for example, the method of Saito and Miura (refer to H. Saito and K. Miura, Biochem. Biophys. Acta, 72, 619 (1963), Text for Bioengineering Experiments, Edited by the Society for Bioscience and Bioengineering, Japan, pp. 97-98, Baifukan, 1992).

Then, the ybjE gene is ligated to a vector DNA operable in the host microorganism to prepare a recombinant DNA. Preferably, vectors autonomously replicable in the host microorganism are used.

Examples of vectors autonomously replicable in *Escherichia coli* include pUC19, pUC18, pHSG299, pHSG399, pHSG398, pACYC184, (pHSG and pACYC are available from Takara Bio), RSF1010, pBR322, pMW219 (pMW is available from Nippon Gene), and so forth.

Examples of vectors which is autonomously replicable in Coryneform bacteria include pAM330 (JP58-67699A), pHM1519 (JP58-77895A), pVK7 (US2003-0175912) and pSFK6 (JP2000-262288A). Moreover, a so-called shuttle vector autonomously replicable in both Escherichia coli and Coryneform bacteria may also be used.

Examples of vectors autonomously replicable in Methylophilus bacteria include RSF1010, and derivatives thereof such as pAYC32 (Chistorerdov, A. Y., Tsygankov, Y. D., Plasmid, 16, pp. 161-167 (1986)), pMFY42 (Gene, 44, p. 53 (1990)), pRK301, and pTB70 (Nature, 287, 396 (1980)).

In order to prepare a recombinant DNA by ligating the ybjE gene and any of the vectors mentioned above, the vector and a fragment containing the ybjE gene are digested with restriction enzymes and ligated, usually by using a ligase such as a T4 DNA ligase.

To introduce a recombinant DNA prepared as described above into a microorganism, any known transformation method reported so far can be employed. For example, treating recipient cells with calcium chloride so as to increase the permeability of DNA, which has been reported for Escherichia coli (Mandel, M. and Higa, A., J. Mol. Biol., 53, 159 (1970)), and using competent cells prepared from growing cells to introduce a DNA, which has been reported for Bacillus subtilis (Duncan, C. H., Wilson, G. A. and Young, F. E., Gene, 1, 153 (1977)) can be employed. In addition to these methods, introducing a recombinant DNA into protoplast- or spheroplast-like recipient cells, which have been reported to be applicable to Bacillus subtilis, actinomycetes, and yeasts (Chang, S, and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)), can be employed. In addition, transformation of Coryneform bacteria can also be performed by the electric pulse method (Sugimoto et al., JP2-207791A).

The copy number of the ybjE gene can also be increased by integrating multiple copies of the gene on a chromosomal DNA of a microorganism. In order to integrate multiple copies of the ybjE gene on a chromosomal DNA of a microorganism, homologous recombination can be performed by targeting a sequence which exists in multiple copies on a chromosomal DNA. Repetitive DNA and inverted repeats at an end of a transposon can be used as a sequence in which multiple copies exist on a chromosomal DNA. Alternatively, as disclosed in JP2-109985A, it is also possible to incorporate the ybjE gene into a transposon, and allow it to be transferred so that multiple copies of the gene are integrated into the chromosomal DNA. Integration of the ybjE gene into the chromosome can be confirmed by southern hybridization using a probe having a partial sequence of the ybjE gene.

Enhancing expression of the ybjE gene can also be attained by either replacing an expression regulatory sequence, including a promoter of the ybjE gene, on a chromosomal DNA or on a plasmid with a stronger one, as described in WO00/18935, amplifying a regulatory factor that increases expression of the ybjE gene, or deleting or attenuating a regulatory factor that reduces expression of the ybjE gene. For example, the lac promoter, trp promoter, trc promoter and so forth are known as strong promoters. Moreover, it is also possible to introduce several nucleotide substitutions into a promoter region for the ybjE gene so that the promoter should be more potent. A method for evaluating potency of promoter and examples of potent promoters are disclosed in Goldstein et al. (Prokaryotic promoters in biotechnology. Biotechnol. Annu. Rev., 1995, 1, 105-128). Furthermore, since it is known that a spacer sequence between the ribosome binding site (RBS) and translation initiation codon, especially, several nucleotides just upstream of the initiation codon, has a great influence on translation efficiency. Therefore, this sequence may be modified. Expression regulatory sequences of ybjE gene may be identified using a vector for promoter identification or genetic analysis software such as GENETYX.

The expression of the ybjE gene is enhanced by such substitution or modification of a promoter. The substitution of an expression regulatory sequence can also be attained by, for example, using a temperature-sensitive plasmid. Examples of a temperature-sensitive plasmid for Coryneform bacteria include p48K and pSFKT2 (JP2000-262288A), pHSC4 (refer to France Patent Laid-open Publication No. 2667875, 1992 and JP5-7491A), and so forth. These plasmids can autonomously replicate at least at a temperature of 25° C., but cannot autonomously replicate at a temperature of 37° C. in Coryneform bacteria. Modifying the expression regulatory sequence may be combined with increasing the copy number of the ybjE gene.

In order to enhance an activity of the protein encoded by the ybjE gene, a mutation which increases an L-amino acid-export ability may be introduced into the ybjE gene. Examples of a mutation that increases activity of the protein encoded by the ybjE gene (YbjE protein) include a mutation in a promoter sequence that increases the transcription of the ybjE gene and a mutation in the coding region of the ybjE gene that increases the specific activity of the YbjE protein.

The microorganism of the present invention is preferably one in which the L-amino acid-export ability is enhanced due to a modification which results in an increase in expression of the ybjE gene. The phrase "L-amino acid-export ability is enhanced" used herein means that when culturing a microorganism which has been modified to enhance expression of the ybjE gene, the amount of L-amino acid exported into the medium by the microorganism is more than that of an L-amino acid exported from a non-modified strain, such as a parent strain or a corresponding wild-type strain. The increase in L-amino acid-export ability is observed by determining the increase in concentration of the L-amino acid in the medium. Furthermore, the increase in L-amino acid-export ability is also observed by determining the decrease in intracellular concentration of the L-amino acid upon introduction of ybjE gene into a microorganism. The amount of L-amino acid exported from the microorganism of the present invention is preferably increased by 10% or more, more preferably 30% or more, particularly preferably 50% or more, when compared to the amount of L-amino acid exported from a non-modified strain. Furthermore, the increase in L-amino acid-export ability is also observed in terms of a decrease in intracellular concentration of the L-amino acid upon introduction of ybjE gene into a microorganism. For example, the intracellular concentration of an L-amino acid can be measured as follows: an appropriate amount of silicon oil having specific gravity of 1.07 is added to a medium containing microbial cells, and cells are collected from the medium by centrifugation, preferably at 12,000 rpm for 2 minutes. Then the cells are treated with 22% perchloric acid (A. Ishizaki et al, Biotech. Tecniq. (1995) Vol 9, No. 6, p 409). Using thus prepared cells, an intracellular concentration of an L-amino acid can be measured. Furthermore, "L-amino acid-export ability" can be examined indirectly by measuring cellular uptake of radiolabeled L-amino acid using everted membrane vesicles (J. Biol. Chem., Vol. 277, Issue 51, 49841-49849). For example, everted membrane vesicles are prepared from cells into which ybjE gene is introduced. Then, ATP or other substrates which provide driving energy are added to the vesicles, and cellular uptake of radiolabeled L-amino acid is measured. Alternatively, "L-amino acid-export ability" may be examined by measuring the rate of the exchange reaction between a non-labeled amino acid and a labeled amino acid in active cells.

Furthermore, the microorganism of the present invention is preferably a microorganism that has become more resistant to an L-amino acid or L-amino acid analogue due to a modification resulting in enhancement of the ybjE gene expression. That is, preferably the microorganism of the present invention is a microorganism that is able to grow in the presence of an L-amino acid or L-amino acid analogue at a concentration which the non-modified strain cannot grow. Cell growth in the presence of the L-amino acid or L-amino acid analogue can be confirmed in a minimal medium containing a high concentration of the L-amino acid or L-amino acid analogue, for example, 0.3 g/L or higher. L-amino acid- or L-amino acid analogue-resistance of the ybjE gene-enhanced strain can be confirmed by measuring the growth of the strain in a minimal medium containing high concentrations of the L-amino acid or L-amino acid analogue, and comparing to the growth of a parent strain or unmodified strain. The method of comparing the growth includes a method of comparing an optical density at 580-660 nm of a medium in which each strain is growing. The concentration of an L-amino acid or L-amino acid analogue which has been added to a medium is not particularly limited so long as it inhibits the growth of an unmodified strain, preferably not less than 0.3 g/L. For example, L-lysine hydrochloride is added at 80 g/L, L-arginine hydrochloride is added at 90 g/L, L-ornithine hydrochloride is added at 45 g/L, L-histidine hydrochloride is added at 30 g/L, L-isoleucine is added at 12 g/L, L-threonine is added at 40 g/L, L-monosodium glutamate acid is added at 15 g/L, L-phenylalanine is added at 8 g/L, L-proline is added at 85 g/L, and L-cysteine is added at 0.3 g/L.

The microorganism of the present invention may be one that has become more resistant to L-lysine or an L-lysine analogue due to the modification which results in enhancing ybjE gene expression. Examples of the L-lysine analogue include oxalysine, lysine hydroxamate, S-(2-aminoethyl)-L-cysteine (AEC), γ-methyllysine, α-chlorocaprolactam, and so forth, but are not limited to these. The L-lysine resistance can be confirmed in the same manner as the aforementioned L-amino acid or L-amino acid analogue resistance.

The microorganism of the present invention may be one that has become more resistant to L-arginine or an L-arginine analogue due to the modification which results in enhancing ybjE gene expression. Examples of the L-arginine analogue include arginine hydroxamate, homoarginine, D-arginine, canavanine, arginine hydroxamate, and so forth. The L-arginine or L-arginine analogue resistance can be confirmed in the same manner as the aforementioned L-amino acid or L-amino acid analogue resistance.

<2> Method for Producing L-Amino Acid

The production method of the present invention comprises culturing the microorganism of the present invention in a medium to produce and cause accumulation of the L-amino acid in the medium or cells of the microorganism, and collecting the L-amino acid from the medium or the cells.

The medium to be used in the present invention may be selected from well-known media conventionally used for fermentative production of L-amino acids using microorganisms. That is, a usual medium that contains a carbon source, nitrogen source, inorganic ions, and if necessary, other organic ingredients may be used. As the carbon source, saccharides such as glucose, sucrose, lactose, galactose, fructose, or starch hydrolysate, alcohols such as glycerol or sorbitol, or organic acids such as fumaric acid, citric acid, or succinic acid can be used. As the nitrogen source, inorganic ammonium salts such as ammonium sulfate, ammonium chloride, or ammonium phosphate, organic nitrogen such as soybean protein hydrolysate, ammonia gas, aqueous ammonia, and so forth can be used. It is desirable to add substances such as vitamin $B_1$ and L-homoserine, yeast extract, and so forth to the medium in appropriate amounts as organic trace nutrients. Other than the above, potassium phosphate, magnesium sulfate, iron ion, manganese ion, and so forth are added in small amounts, if necessary. The medium used for the present invention may be a natural medium or a synthetic medium, so long as it contains a carbon source, nitrogen source, inorganic ions, and if necessary, other organic ingredients.

The culture is preferably carried out under aerobic conditions for 1 to 7 days. The culture temperature is preferably controlled to 24° C. to 37° C., and the pH is preferably controlled to 5 to 9 during the culture. Inorganic or organic, acidic or alkaline substances as well as ammonia gas and so forth can be used to adjust the pH. L-amino acids can be collected from the fermentation broth usually by a combination of well-known techniques, such as by utilizing ion exchange resins, precipitation, and other techniques. When an L-amino acid accumulates in cells, for example, the cells can be disrupted by ultrasonication, the disrupted cells can be removed by centrifugation, and the L-amino acid can be collected from the obtained supernatant using an ion-exchange resin or the like.

If methanol is used as the major carbon source in the production method of the present invention, the cost is lowered, and therefore microorganisms such as *Methylophilus* and *Methylobacillus* bacteria, which have an ability to assimilate methanol, are preferable. In this case, the culture can be performed according to a culture method typical for a usual methanol-assimilating microorganism (refer to, for example, WO00/61723, JP2001-120269A etc.). When the culture is performed by using methanol as a major carbon source, methanol is preferably added to the medium at a concentration of 0.001 to 30%. For the culture of a methanol-assimilating microorganism, ammonium sulfate and so forth are preferably added to the medium and used as a nitrogen source. In addition, trace amount components such as potassium phosphate, sodium phosphate, magnesium sulfate, ferrous sulfate, and manganese sulfate are preferably added in small amounts.

The culture of a methanol-assimilating microorganism is preferably performed under aerobic conditions with shaking or agitation for aeration, at a pH range of 5 to 9, and at a temperature of 20 to 45° C., usually for 24 to 120 hours. The L-amino acids can be collected from the culture by a combination of well-known techniques, such as ion exchange resins, precipitation, and other techniques. Collection of the L-amino acids from cells can be performed in the same manner as described above.

EXAMPLES

Hereinafter, the present invention will be explained more specifically with reference to the following non-limiting examples. The reagents used in the following examples were obtained from Wako Pure Chemicals or Nakarai Tesque unless otherwise indicated. The composition of the medium used in each example is shown below. pH was adjusted with NaOH or HCl for all of the media.

L Medium:

| | |
|---|---|
| Bacto trypton (Difco) | 10 g/L |
| Yeast extract (Difco) | 5 g/L |
| Sodium chloride | 10 g/L |
| pH 7.0 | |

These were subjected to steam sterilization at 120° C. for 20 minutes.

L agar Medium:

| | |
|---|---|
| L medium | |
| Bacto agar | 15 g/L |

These were subjected to steam sterilization at 120° C. for 20 minutes.

Minimal Medium: (Following Molecular Cloning Vol. 3)

| | |
|---|---|
| 5 * M9 salts | 200 ml |
| 20% Glucose | 20 ml |
| 1 M Magnesium sulfate | 2 ml |
| 1 M Calcium chloride | 0.1 ml |
| Filling up to 1 L, adjusted pH | 7.0 |

5*M9 Salts

| | |
|---|---|
| Disodium phosphate | 64 g |
| Potassium phosphate | 15 g |
| Sodium chloride | 2.5 g |
| Ammonium chloride | 5.0 g |
| Filling up to 1 L | |

After filling up to 1 L, these were subjected to steam sterilization at 115° C. for 10 minutes, and L-lysine was added at an appropriate time.

Minimal Agar Medium:

| | |
|---|---|
| Minimal medium | |
| Bacto agar | 15 g/L |

These were subjected to steam sterilization at 115° C. for 10 minutes.

L-Lysine Production Medium for *Escherichia* Bacterium:

| | |
|---|---|
| Glucose | 40 g/L |
| Ammonium sulfate | 24 g/L |
| Potassium dihydrogenphosphate | 1.0 g/L |
| Magnesium sulfate heptahydrate | 1.0 g/L |
| Iron(IV) sulfate heptahydrate | 0.01 g/L |
| Manganese(IV) sulfate heptahydrate | 0.01 g/L |
| Yeast extract | 2.0 g/L |
| pharmacopeia calcium carbonate | 30 g/L | pH was adjusted to 7.0 with potassium hydroxide, and the components were subjected to steam sterilization at 115° C. for 10 minutes, except glucose and $MgSO_4 \cdot 7H_2O$, which were separately sterilized. As an antibiotic, 50 mg/L of chloramphenicol was added.

L-Arginine Production Medium for *Escherichia* Bacterium:

| | |
|---|---|
| Glucose | 60 g/L |
| (separately sterilized) | |
| Magnesium sulfate heptahydrate | 1 g/L |
| (separately sterilized) | |
| Ammonium sulfate | 25 g/L |
| Potassium dihydrogenphosphate | 2 g/L |
| Yeast extract (Difco) | 5 g/L |
| Vitamin B1 | 0.1 mg/L |
| pH 7.2 | |
| pharmacopeia calcium carbonate | 25 g/L |
| (separately sterilized) | | pH was adjusted to 7.2 with potassium hydroxide, and the components were subjected to steam sterilization at 115° C. for 10 minutes, except glucose and $MgSO_4 \cdot 7H_2O$, which were separately sterilized. As an antibiotic, 50 mg/L of chloramphenicol was added.

L-Lysine Production Medium for *Methylophilus* Bacterium (SEII Medium):

| | |
|---|---|
| Potassium dihydrogenphosphate | 1.9 g/L |
| Sodium dihydrogenphosphate | 1.56 g/L |
| Magnesium sulfate | 0.2 g/L |
| Ammonium sulfate | 5 g/L |
| Copper sulfate pentahydrate | 5 µg/L |
| Manganese(IV) sulfate pentahydrate | 25 µg/L |
| Zinc(IV) sulfate heptahydrate | 23 µg/L |
| Calcium(II) chloride dihydrate | 72 mg/L |
| Iron(II) chloride hexahydrate | 9.7 mg/L |
| Calcium carbonate (Kanto Kagaku) | 30 g/L |
| Methanol | 2% (vol/vol) |
| pH | 7.0 |

The components other than methanol were subjected to steam sterilization at 121° C. for 15 minutes, and methanol was added after the components were sufficiently cooled. This medium was prepared with reference to Journal of General Microbiology (1989) 125, 135, 3153-3164, Silman N. J., Carver M. A. & Jones C. W. Instead of ammonium sulfate, 1.18 g of acetamide was used, and calcium chloride was added at a concentration of 72 mg/L.

SEII Agar Medium:

| | |
|---|---|
| Potassium dihydrogenphosphate | 1.9 g/L |
| Sodium dihydrogenphosphate | 1.56 g/L |
| Magnesium sulfate | 0.2 g/L |
| Ammonium sulfate | 5 g/L |
| Copper sulfate pentahydrate | 5 µg/L |
| Manganese(IV) sulfate pentahydrate | 25 µg/L |
| Zinc(IV) sulfate heptahydrate | 23 µg/L |
| Calcium(II) chloride dihydrate | 72 mg/L |
| Iron(II) chloride hexahydrate | 9.7 mg/L |
| Calcium carbonate (Kanto Kagaku) | 30 g/L |
| Methanol | 2% (vol/vol) |
| pH | 7.0 |
| Bacto agar (Difco) | 15 g/L |

The components other than methanol were subjected to steam sterilization at 121° C. for 15 minutes, and methanol was added after the components were sufficiently cooled.

CM2S Medium for *Coryneform* Bacterium:

| | |
|---|---|
| Polypeptone | 10 g/L |
| Yeast Extract | 10 g/L |
| Sodium chloride | 5 g/L |
| Sucrose | 5 g/L |
| DL-methionine | 0.1 g/L | pH was adjusted to 7.2 with potassium hydroxide, and the components were subjected to steam sterilization at 120° C. for 30 minutes. When the medium was used for plate culture, 20 g/L of agar was added.

L-Lysine Production Medium for *Coryneform* Bacterium:

| | |
|---|---|
| Glucose | 100 g/L |
| Ammonium sulfate | 55 g/L |
| Soy bean hydrolysate | 1.05 g of total nitrogen/L |
| Potassium dihydrogenphosphate | 1.0 g/L |
| Magnesium sulfate heptahydrate | 1.0 g/L |
| Iron(IV) sulfate hexahydrate | 0.01 g/L |
| Manganese(IV) sulfate pentahydrate | 0.01 g/L |
| Magnesium sulfate | 0.2 g/L |
| GD113 | 0.05 ml/L |
| pharmacopeia calcium carbonate (separately sterilized) | 50 g/L | pH was adjusted to 7.5 with potassium hydroxide, and the components were subjected to steam sterilization at 115° C. for 10 minutes, except glucose and $MgSO_4 \cdot 7H_2O$, which were separately sterilized.

Example 1

Screening of the L-Lysine-Export Gene

The search for an L-lysine-export gene was carried out as follows.

<1-1> Construction of *Escherichia coli* Strain into which Plasmid Library is Introduced Chromosomal DNA was extracted in a conventional manner from a strain obtained by deleting lysA (diaminopimelate decarboxylase gene) in the MG1655 (ATCC 47076) strain. 2 to 4 kbp fragments obtained by partial digestion of the chromosomal DNA with the restriction enzyme Sau3AI were introduced into each of the vectors pTWV229 (Takara Bio), pSTV28 (Takara Bio), and pMW118 (Nippon Gene), all of which were digested with BamHI in advance, and thereby plasmid libraries were obtained. Each of these plasmid libraries was introduced into the MG1655 strain by electroporation.

<1-2> Screening of L-Lysine-Resistance Gene

The MG1655 strains introduced with the plasmid libraries were selected in the L medium based on ampicillin resistance for the pTWV229-introduced strain, chloramphenicol resistance for the pSTV28-introduced strain, and ampicillin resistance for the pMW118-introduced strain. About 80,000 transformed colonies in total were obtained. These transformants were plated on the minimal medium containing 60 g/L of lysine hydrochloride, on which the MG1655 strain can minimally form very few colonies, if any.

After culturing at 37° C. for 36 hours, about 50 colonies that appeared on the medium containing high concentrations of lysine were selected as candidate lysine-resistant strains. In order to determine the sequences inserted into the vectors of the candidate lysine-resistant strains, PCR was performed by using synthetic oligonucleotides having a sequence of SEQ ID NO: 3 (M13 Forward primer), and SEQ ID NO: 4 (M13 Reverse primer), which are complementary to the DNA sequence located around the multi-cloning site of the plasmid, and the sequences of the amplified fragments were determined.

As a result of the determination of the nucleotide sequences, it was found that almost all the fragments contained ybjE, located at the numbers 913181 to 914128, in the L-lysine-resistant strains.

The predicted amino acid sequence from the ybjE gene sequence was analyzed. When the sequence of the protein was analyzed for hydrophobic properties, it was found that the protein is highly hydrophobic. Therefore, it was suggested that the protein encoded by ybjE was a membrane protein and might be involved in amino acid export.

Example 2

Effect of ybjE Gene Amplification in *Escherichia coli*

<2-1> Construction of a Plasmid for ybjE Amplification and Introduction Thereof into *Escherichia coli*

Then, in order to study the effect of amplification of the ybjE gene, a vector for amplifying ybjE was constructed and introduced into MG1655. The total nucleotide sequence of the chromosome of *Escherichia coli* (*Escherichia coli* K-12 strain) has been reported (Science, 277, 1453-1474 (1997), and therefore the synthetic oligonucleotide of SEQ ID NO: 5, which has a sequence complementary to the sequence of nucleotide numbers 4085 to 4104 of GenBank Accession No. AE000189, and the synthetic oligonucleotide of SEQ ID NO: 6 which corresponds to the sequence of nucleotide numbers 2689 to 2708 of the same nucleotide sequence, were prepared on the basis of the nucleotide sequence of the ybjE gene reported in the above literature and used as the 5' primer and 3' primer, respectively, to perform PCR. The chromosomal DNA of *Escherichia coli* MG1655 strain was used as a template.

The obtained PCR product was ligated to the vector pSTV28, which had been (Takara Bio) digested with SmaI, to construct a plasmid pSYBJE for amplification of ybjE. The construction scheme is shown in FIG. 1. A plasmid in which the ybjE gene was ligated in the forward direction with respect to the lac promoter was designated pSYBJE1, and a plasmid in which it was ligated in the reverse direction was designated pSYBJE2.

The plasmids for ybjE gene amplification, pSYBJE1, pSYBJE2, and a control plasmid pSTV28 (Takara Bio) were each introduced into MG1655 (ATCC 47076) in a conventional manner. Transformants were selected based on chloramphenicol resistance, and the strain introduced with pSYBJE1 was designated MG1655/pSYJE1, the strain introduced with pSYBJE2 was designated MG1655/pSYBJE2, and the strain introduced with pSTV28 was designated MG1655/pSTV28.

<2-2> Effect of ybjE Gene Amplification in *Escherichia* Bacterium

Effect of amplification of the ybjE gene on the resistance of the *Escherichia coli* MG1655 strain to various amino acids was examined using the pSYBJE1- or pSYBJE2-introduced strain. The MG1655/pSYBJE1, the MG1655/pSYBJE2, and the control MG1655/pSTV28 strains were each inoculated into 5 mL of L medium containing 50 µg/mL of chloramphenicol and cultured for about 6 hours using a culturing apparatus with shaking by reciprocal movement. The culture broth in which the cells had proliferated to a turbidity of OD600=about 1.0 was centrifuged, and then the cells were washed twice with M9 minimal medium. Next, the cells were inoculated into M9 minimal medium containing 50 μg/mL of chloramphenicol and M9 minimal medium containing 80 g/L of lysine hydrochloride to a turbidity of OD600=0.05, and cultured for about 70 hours.

Figure 2:
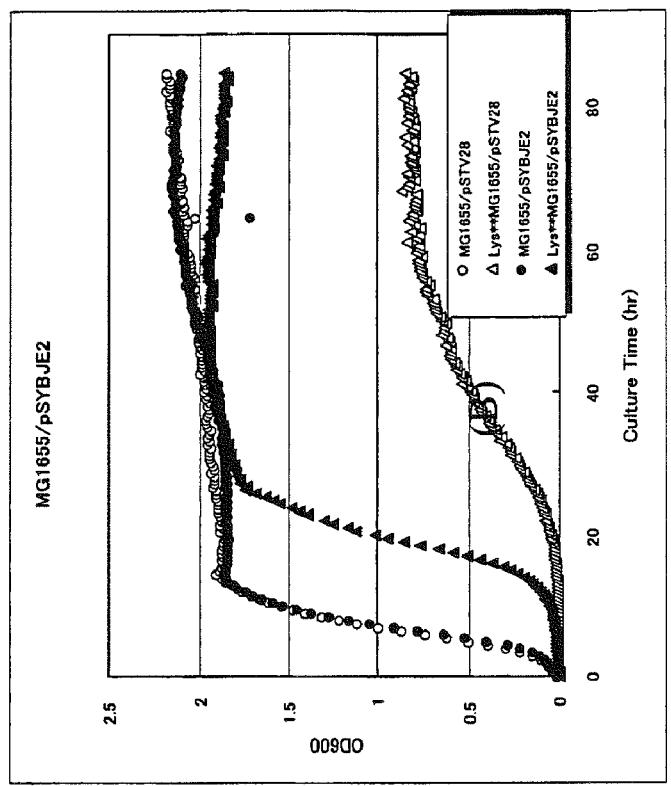
FIG. 2 shows growth curves for a control strain and ybjE gene-amplified strain of *Escherichia coli* in the presence of high concentrations of L-lysine.
Figure 2:
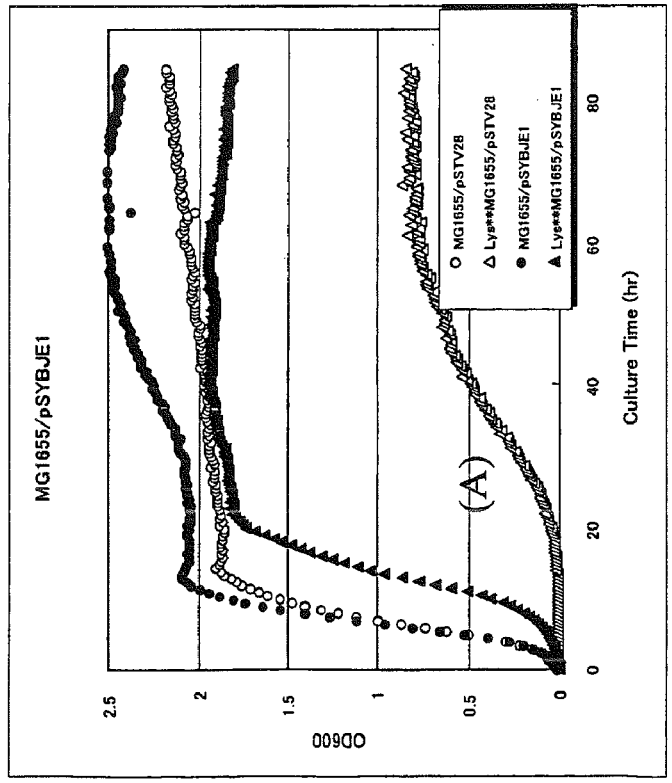

The results are shown in FIG. 2, which shows that enhancing ybjE gene expression improved the growth rate at an early stage, as well as the cell division rate during the logarithmic growth phase, in the presence of high concentrations of L-lysine as compared to the control strain.

Example 3

Effect of ybjE Gene Disruption on Amino Acid Resistance of an *Escherichia* Bacterium <3-1> Construction of a ybjE Gene-Disrupted Strain Deletion of the ybjE gene was attained by the method developed by Datsenko and Wanner called "Red-driven integration" (Proc. Natl. Acad. Sci. USA, 2000, vol. 97, No. 12, pp. 6640-6645). According to this method, a PCR product was obtained using a synthetic oligonucleotide containing an object gene at the 5' side and an antibiotic resistance gene at the 3' side. Using this method, a gene-disrupted strain can be constructed in a single step. According to this method, primers complementary to the regions around the ybjE gene or the gene imparting antibiotic resistance to a template plasmid were designed, and PCR product of endogenous ybjE gene was obtained. The PCR product can be obtained by using the plasmid pACYC184 (NBL Gene Sciences Ltd., U.K., GenBank/EMBL Accession Number X06403) as a template and synthetic oligonucleotides having a sequence of SEQ ID NOS: 7 and 8 as primers.

The amplified PCR product was purified on an agarose gel and used for electroporation of the *Escherichia coli* MG1655 strain, which harbors plasmid pKD46 having temperature-sensitive replication ability. Plasmid pKD46 (Proc. Natl. Acad. Sci. USA, 2000, vol. 97, No. 12, pp. 6640-6645) contains a 2154-nucleotide DNA fragment of λ phage containing genes of the λ Red homologous recombination system (λ, β, exo genes), which are controlled by arabinose-inducible ParaB promoter (GenBank/EMBL Accession No. J02459, 31088th to 33241st nucleotides). Plasmid pKD46 is necessary to incorporate the PCR product into the chromosome of the MG1655 strain.

Competent cells for electroporation were prepared as follows. *Escherichia coli* MG1655 strain was cultured overnight at 30° C. in LB medium containing 100 mg/L of ampicillin, and then diluted 100-fold with 5 mL of SOB medium (Molecular Cloning A Laboratory Manual, 2nd Edition, Sambrook, J. et al., Cold Spring Harbor Laboratory Press (1989)) containing ampicillin and L-arabinose (1 mM). The diluted cells were grown at 30° C. with aeration until OD600 had become about 0.6, and then concentrated 100-fold and washed three times with ice-cooled deionized water so that the cells could be used for the electroporation. The electroporation was performed by using 70 μl of the competent cells and about 100 ng of the PCR product. The cells after electroporation were added into 1 mL of the SOC medium (Molecular Cloning A Laboratory Manual, 2nd Edition, Sambrook, J. et al., Cold Spring Harbor Laboratory Press (1989)), cultured at 37° C. for 2.5 hours, and then plated onto the L agar medium at 37° C. In this way, Cm (chloramphenicol)-resistant recombinant strains were selected. Then, in order to cure the pKD46 plasmid, the cells were subcultured twice at 42° C. on L agar medium containing Cm (chloramphenicol), and ampicillin resistance of the obtained colonies was examined. In this way, ampicillin-sensitive strains in which pKD46 was cured were obtained.

Disruption of the ybjE gene in the mutant strain, which could be identified by chloramphenicol-resistance, was confirmed by PCR. The length of the PCR product obtained by using DNA in cells of the ybjE gene-disrupted strain MG1655ΔybjE::cat, was longer than that obtained for a wild-type strain. Thus, it was confirmed that the chloramphenicol-resistance gene was inserted into the ybjE gene, and it was confirmed that the ybjE gene had been disrupted. The ybjE-disrupted strain having the chloramphenicol-resistance gene inserted was designated MG1655ΔybjE::Cm.

<3-2> Confirmation of Amino Acid Resistance of the ybjE Gene-Deficient Strain

The influence of the ybjE gene-deficient strain MG1655ΔybjE::Cm on amino acid resistance was examined. Culture broths (600 OD~1.0) obtained by culturing the MG1655ΔybjE::Cm and the control MG1655 strain in L medium for about 6 hours on a culturing apparatus with shaking by reciprocal movement were centrifuged. Then, the cells were washed twice with M9 minimal medium and inoculated into M9 minimal medium or M9 minimal medium containing 80 g/L of lysine hydrochloride to OD600=0.05, and cultured for about 70 hours. Then, the growth was examined.

Figure 3:
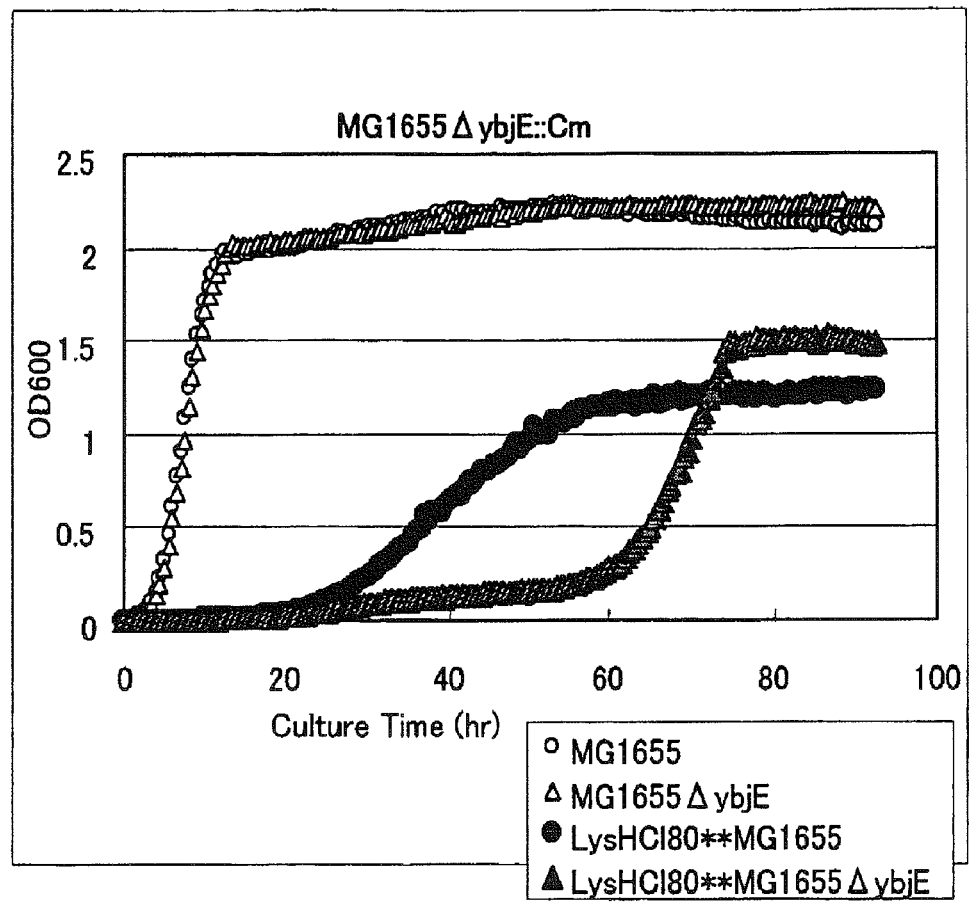
FIG. 3 shows growth curves for a control strain and ybjE gene-disrupted strain of *Escherichia coli* in the presence of high concentrations of L-lysine.

The results are shown in FIG. 3. As shown in FIG. 3, the deletion of the ybjE gene reduced the growth at an early stage when in the presence of high concentrations of L-lysine, as compared to the control strain. From this result and the results of Example 2, it was revealed that the ybjE gene imparted resistance to L-lysine.

Example 4

The Effect of ybjE Amplification on L-Lysine Production of an *Escherichia* Bacterium As an L-lysine-producing strain of *Escherichia coli*, the WC1-96 strain (AJ13069 (FERM BP-5252), WO96/17930) was used, which is AEC (S-(2-aminoethyl)cysteine) resistant.

The WC1-96 strain was transformed with plasmid pSYBJE1 for ybjE amplification. Plasmid pSTV28 (Takara Bio) was transformed separately as a control (as in Example 2). Thereby, chloramphenicol-resistant strains were obtained. Introduction of the plasmids was confirmed, and the strain introduced with the plasmid pSYBJE1 was designated WC196/ybjE, and the strain introduced with the control plasmid pSTV28 was designated WC196/pSTV28.

The WC196/ybjE and WC196/pSTV28 strains were each cultured at 37° C. in L medium containing 50 mg/L of chloramphenicol until OD600 became about 0.6. Then, an equal volume of 40% glycerol solution was added to each culture broth, stirred, and then divided into appropriate volumes, and stored at −80° C. These are referred to herein as glycerol stocks.

The glycerol stocks of these strains were thawed, and 100 μL of each stock was uniformly plated on an L plate containing 50 mg/L of chloramphenicol and incubated at 37° C. for 24 hours. About ⅛ of the cells collected from the plate were inoculated into 20 mL of fermentation medium (M9 minimal medium) containing 50 mg/L of chloramphenicol in a 500-mL Sakaguchi flask, and cultured at 37° C. for 27 hours on a culturing apparatus with shaking by reciprocal movement. After the culture, the amount of lysine which had accumulated in the medium was measured using Biotech Analyzer AS210 (Sakura Seiki). As for the L-lysine concentration in the cells, a suitable volume of the culture broth was added to silicone oil having a specific gravity of 1.07 and cells were collected by centrifugation at 12000 rpm for 2 minute. Then, the collected cells were disrupted by treatment with 22% perchloric acid, and the concentration of lysine was measured.

The accumulation and yield of L-lysine as well as the ratio of extracellular to intracellular lysine concentration after 24 hours are shown in Table 1. The ratio of extracellular to intracellular lysine concentration indicated with * was determined by dividing extracellular lysine concentration (mg/g of dry cell weight) by intracellular lysine concentration (mg/g of dry cell weight). As shown in Table 1, the WC196/pSYBJE1 strain accumulated a larger amount of lysine compared to the WC196/pSTV28 strain, which had not been introduced with the ybjE gene. Furthermore, in the WC196/pSYBJE1 strain introduced with the ybjE gene, the extracellular L-lysine concentration was increased relative to the intracellular L-lysine concentration due to a marked decrease of the intracellular lysine concentration compared to the control WC196/pSTV28 strain, and thus it was suggested that the ybjE gene was an L-lysine-export gene.

TABLE 1

| Strain | L-Lysine accumulation (g/L) | L-Lysine yield (%) | Ratio of Extra- to intracellular lysine concentration * |
|---|---|---|---|
| WC196 | 1.3 | 3.3 | 17.7 |
| WC196/pSTV28 | 0.9 | 2.3 | 12.2 |
| WC196/pSYBJE1 | 7.6 | 19 | 35.3 |

Example 5

The Effect of ybjE Amplification on L-Arginine Production of an *Escherichia* Bacterium It was observed that both the accumulation and yield of L-lysine were increased in the ybjE gene-amplified strain as compared to the control strain. The effect of ybjE amplification on production of L-arginine, which is a known basic amino acid like L-lysine, was also examined. As an L-arginine-producing bacterium of *Escherichia coli*, the 237 strain having feedback inhibition of N-acetylglutamate synthase released (VKPM B-7925, Russian Patent Application No. 2000117677) was used.

<5-1> Preparation of ybjE Gene-Amplified Strain of *Escherichia coli* 237 Strain By using the same method as in Example 4, ybjE gene-amplified 237/pSYBJE1 strain and a control 237/pSTV28 strain were prepared.

<5-2> Production of L-Arginine

By using the media, culture methods, and analysis methods as described below, the effect of ybjE gene amplification on L-arginine production was examined. As a pre-culture, 100 μL of glycerol stock was inoculated on L agar medium, then uniformly plated on an L plate containing 50 mg/L of chloramphenicol, and incubated at 32° C. for 24 hours. About ⅛ of the cells collected from the plate were inoculated into 20 mL of the arginine production medium and cultured at 32° C. for 90 hours. The culture of the plasmid-introduced strains was performed with addition of chloramphenicol.

1 ml of culture broth was picked up during culture, and glucose concentration and L-arginine accumulation in the cells and the culture broth were measured. To determine glucose concentration and L-arginine concentration in the culture broth, the culture broth was centrifuged at 15,000 rpm for 5 minutes, the obtained supernatant was diluted appropriately with water, and the concentrations were measured in the diluted supernatant by using a Biotech Analyzer (Sakura Seiki) and an Amino Acid Analyzer L-8500 (Hitachi Instrument Service). To determine the L-arginine concentration in the cells, a suitable volume of culture broth was added to silicone oil having a specific gravity of 1.07 and centrifuged at 12000 rpm for 2 minutes, then the collected cells were disrupted by a treatment with 22% perchloric acid, and the L-arginine concentration was measured. The accumulation and yield of L-arginine as well as the ratio of extracellular to intracellular L-arginine concentration after 90 hours are shown in Table 2. The extracellular to intracellular ratio indicated with * was determined by dividing extracellular L-arginine concentration (mg/g of dry cell weight) by intracellular L-arginine concentration (mg/g of dry cell weight).

TABLE 2

L-Arginine production with the ybjE gene-amplified strain

| Strain | L-Arginine accumulation (g/L) | L-Arginine yield (%) | Ratio of Extra- to intracellular arginine concentration * |
|---|---|---|---|
| 237/pSTV28 | 0.8 | 1.7 | 23.0 |
| 237/pSYBJE1 | 1.7 | 3.6 | 25.6 |

It was observed that the accumulation and yield of L-arginine were increased in the ybjE gene-amplified strain as compared to the control strain. In addition, the ratio of extracellular to intracellular arginine concentration was also increased. Thus, it was suggested that the gene was also involved in the export of L-arginine.

Example 6

The Effect of Introducing the ybjE Gene Derived from an *Escherichia* Bacterium into a *Methylophilus* Bacterium <6-1> Construction of Plasmid pRSybjE for ybjE Amplification In order to introduce the ybjE gene into a *Methylophilus* bacterium, the known plasmid pRS (JP 3-501682A) was used to construct a plasmid pRSybjE for expression of ybjE. pRS is a plasmid having a vector segment of the pVIC40 plasmid, which is (WO90/04636, JP 3-501682A) obtained by deleting a DNA region coding for the threonine operon. The plasmid pVIC40 is derived from the broad host spectrum vector plasmid pAYC32 (Chistorerdov, A. Y., Tsygankov, Y. D., Plasmid, 1986, 16, 161-167), which is a derivative of RSF1010.

First, a plasmid pRStac which contains the tac promoter was constructed from pRS according to the scheme shown in FIG. 3 and as follows. The pRS vector was digested with the restriction enzymes EcoRI and PstI, added to a phenol/chloroform solution, and mixed to terminate the reaction. After the reaction mixture was centrifuged, the upper layer was collected, and DNAs were collected by ethanol precipitation and separated on a 0.8% agarose gel. A DNA fragment of about 8 kilobase pairs (hereinafter "kbp") was collected by using EASY TRAP Ver. 2 (DNA collection kit, Takara Bio). Alternatively, the tac promoter region was amplified by PCR using the pKK223-3 plasmid (expression vector, Pharmacia)

as a template and primers having a sequence of SEQ ID NOS: 16 and 17 (a cycle consisting of denaturation at 94° C. for 20 seconds, annealing at 55° C. for 30 seconds, and extension reaction at 72° C. for 60 seconds was repeated for 30 cycles). Pyrobest DNA polymerase (Takara Bio) was used for PCR. The amplified DNA fragment containing the tac promoter was purified using PCR prep (Promega) and then digested with the restriction enzymes EcoRI and EcoT22I, recognition sites thereof had been designed in the primers. Then, the reaction mixture was added to a phenol/chloroform solution, and mixed to terminate the reaction. After the reaction mixture was centrifuged, the upper layer was collected, and DNAs were collected by ethanol precipitation and separated on a 0.8% agarose gel. A DNA fragment of about 0.15 kbp was collected by using EASY TRAP Ver. 2.

The digestion product of the pRS vector and the tac promoter region fragment prepared as described above were ligated by using DNA Ligation Kit Ver. 2 (Takara Bio). This ligation reaction solution was used to transform *Escherichia coli* (*Escherichia coli* JM109 competent cells, Takara Bio). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture by the alkali-SDS method, and the structure of each plasmid was confirmed by digestion with restriction enzymes. A plasmid in which the transcription direction of the streptomycin resistance gene and the tac promoter were the same was selected, and designated pRStac.

pRStac obtained as described above was digested with Sse8387I (Takara Bio), and mixed with a phenol/chloroform solution to terminate the reaction. After the reaction mixture was centrifuged, the upper layer was collected, and DNAs were collected by ethanol precipitation followed by blunt-ending with a DNA Blunting Kit.

Furthermore, pSYBJE1 as described above was digested with the restriction enzyme PvuII, and mixed with a phenol/chloroform solution to terminate the reaction. After the reaction mixture was centrifuged, the upper layer was collected, and DNAs were collected by ethanol precipitation and separated on a 0.8% agarose gel. A DNA fragment of about 1.5 kbp containing the lac promoter and the ybjE gene was collected using EASY TRAP Ver. 2 (DNA collection kit, Takara Bio).

Figure 4:
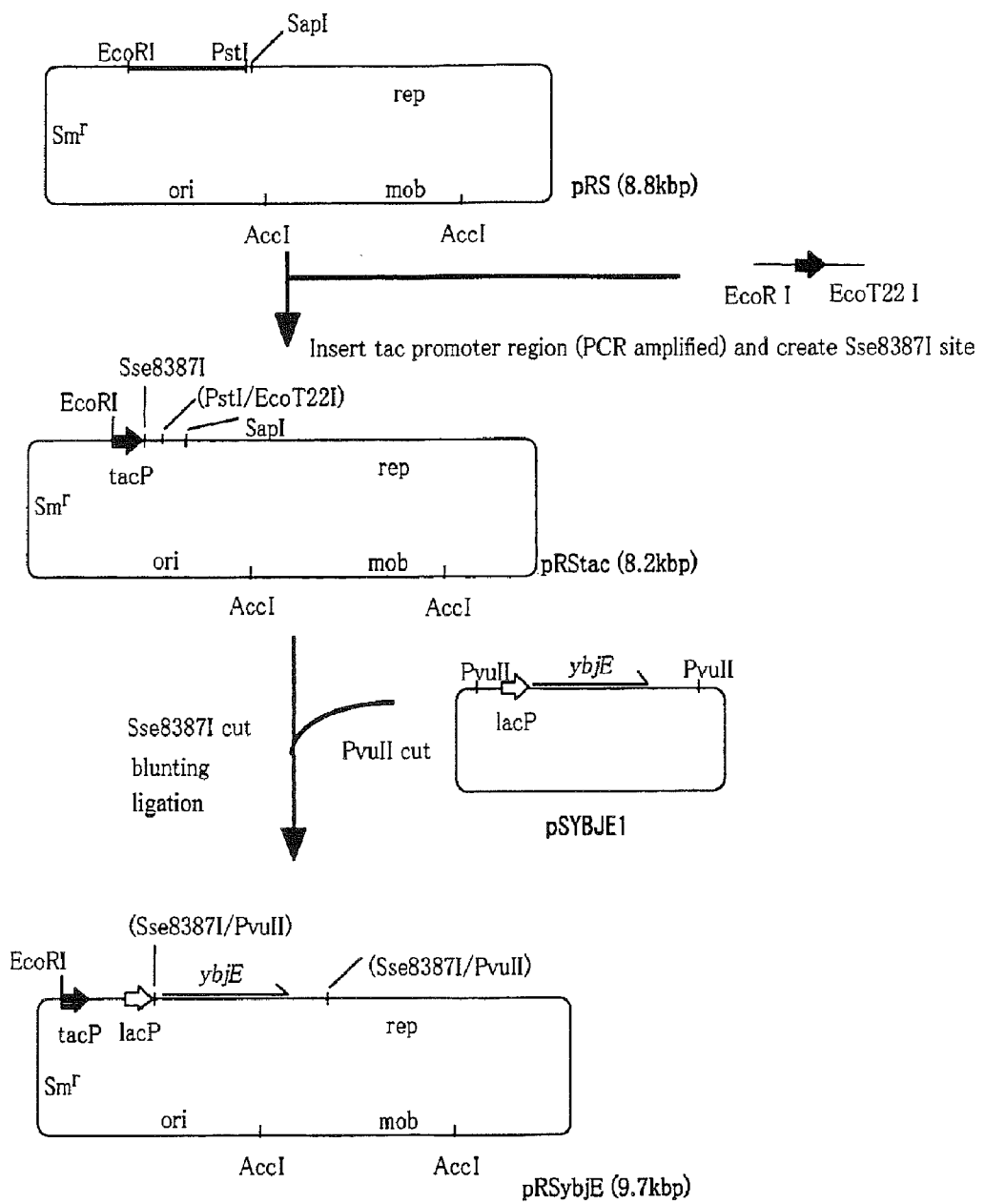
FIG. 4 shows a construction scheme of a plasmid for amplification of the ybjE gene in methanol-assimilating bacteria.

The digestion product of the pRStac vector and the ybjE gene region fragment prepared as described above were ligated together using DNA Ligation Kit Ver. 2 (Takara Bio). This ligation reaction solution was used to transform *Escherichia coli* (*Escherichia coli* JM109 competent cells, Takara Bio). The cells were plated on LB agar medium containing 20 mg/L of streptomycin and incubated overnight at 37° C. The colonies that appeared on the agar medium were inoculated into LB liquid medium containing 20 mg/L of streptomycin and cultured at 37° C. for 8 hours with shaking. Plasmid DNA was extracted from each culture broth by the alkali-SDS method, and the structure of each plasmid was confirmed by digestion with restriction enzymes and DNA sequencing to select pRSybjE (FIG. 4). In the pRSybjE plasmid, the ybjE gene is located so that it is transcribed in the same direction as the tac promoter.

<6-2> The Introduction of pRSybjE into a *Methylophilus* Bacterium pRSybjE obtained as described above was introduced into *Methylophilus methylotrophus* AS1 strain (NCIMB10515) by electroporation (Canadian Journal of Microbiology, 43, 197 (1997)). In addition, pRS was also introduced into the AS1 strain as a control. Transformants were obtained for pRSybjE and pRS based on streptomycin resistance.

The *Methylophilus methylotrophus* AS1 strain harboring pRS or pRSybjE (AS1/pRS, AS1/pRSybjE) was plated on an SEII plate containing 20 mg/L of streptomycin and cultured overnight at 37° C. Then, the cells from about 0.3 cm$^2$ of the medium surface were scraped, inoculated into SEII production medium (20 mL) containing 20 mg/L of streptomycin and cultured at 37° C. for 34 hours with shaking. After completion of the culture, the cells were removed by centrifugation, and the L-lysine concentration in the culture supernatant was determined by using an amino acid analyzer (Nihon Bunko, high performance liquid chromatography). The results are shown in Table 3.

TABLE 3

| Strain | Production amount of L-lysine (g/L) | Production amount of L-arginine (g/L) |
| --- | --- | --- |
| AS1/pRS | <0.01 | <0.01 |
| AS1/pRSybjE | 0.70 | 0.14 |

As a result of the amplification of the ybjE gene, accumulated amounts of L-lysine and L-arginine were markedly increased compared to the control AS1/pRS strain. Thus, it was suggested that ybjE also functions in basic L-amino acid export in *Methylophilus methylotrophus*.

Example 7

Evaluation of *Methylophilus methylotrophus* in which a Gene Encoding Feedback Inhibition-Released Type of Dihydrodipicolinate Synthase and ybjE Gene are Introduced Because it was found that the introduction of the ybjE gene promoted export of L-lysine in the *Methylophilus methylotrophus* AS1 strain, an activity of L-lysine biosynthetic enzyme was enhanced in the ybjE gene-introduced strain to attempt further improvement of the L-lysine production.

<7-1> Construction of Plasmid pRSdapA Containing a Gene Encoding Dihydrodipicolinate Synthase Resistant to Feedback Inhibition by L-Lysine A plasmid containing a gene encoding dihydrodipicolinate synthase resistant to feedback inhibition by L-lysine (referred to as "dapA*" hereinafter) was prepared according to the construction scheme shown in FIG. 5.

pRStac prepared in Example 6 was digested with Sse8387I and XbaI and mixed with a phenol/chloroform solution to terminate the reaction. After the reaction mixture was centrifuged, the upper layer was collected, and DNAs were collected by ethanol precipitation and separated on a 0.8% agarose gel. As a result, a DNA fragment of about 8.2 kbp was collected.

The dapA* gene fragment was amplified by PCR using the plasmid RSFD80 (refer to U.S. Pat. No. 6,040,160) containing dapA* gene as a template and the primers having SEQ ID NOS: 14 and 15 (denaturation at 94° C. for 20 seconds, annealing at 55° C. for 30 seconds, and extension reaction at 72° C. for 60 seconds). Pyrobest DNA polymerase (Takara Bio) was used for PCR. The obtained dapA* fragment was purified by using PCR prep (Promega) and then digested with restriction enzymes Sse8387I and XbaI. The reaction solution was mixed with a phenol/chloroform solution to terminate the reaction. After the reaction mixture was centrifuged, the upper layer was collected, and DNAs were collected by ethanol precipitation and separated on 0.8% agarose gel. As a result, a DNA fragment of about 1.0 kbp was collected.

The digestion product of the pRStac vector and the dapA* gene fragment prepared as described above were ligated to each other by using DNA Ligation Kit Ver. 2 (Takara Bio). This ligation reaction solution was used to transform *Escherichia coli* cells (*Escherichia coli* JM109 competent cells, Takara Bio). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture by the alkali-SDS method, and the structure of each plasmid was confirmed by digestion with restriction enzymes and DNA sequencing to select a pRSdapA plasmid. In the pRSdapA plasmid, the dapA* gene was placed so that it is transcribed in the same direction as the tac promoter.

The *Escherichia coli* JM109 strain transformed with the pRSdapA plasmid was designated AJ13831, and this strain was deposited at the independent administrative agency, National Institute of Advanced Industrial Science and Technology, International Patent Organism Depositary on Jun. 4, 2001 and received an accession number of FERM P-18370. Then, the deposit was converted to an international deposit under the provisions of the Budapest Treaty on May 13, 2002, and received an accession number of FERM BP-8041. Therefore, the pRSdapA plasmid can also be obtained from this strain.

<7-2> Construction of Plasmid Containing ybjE and dapA*

Figure 5:
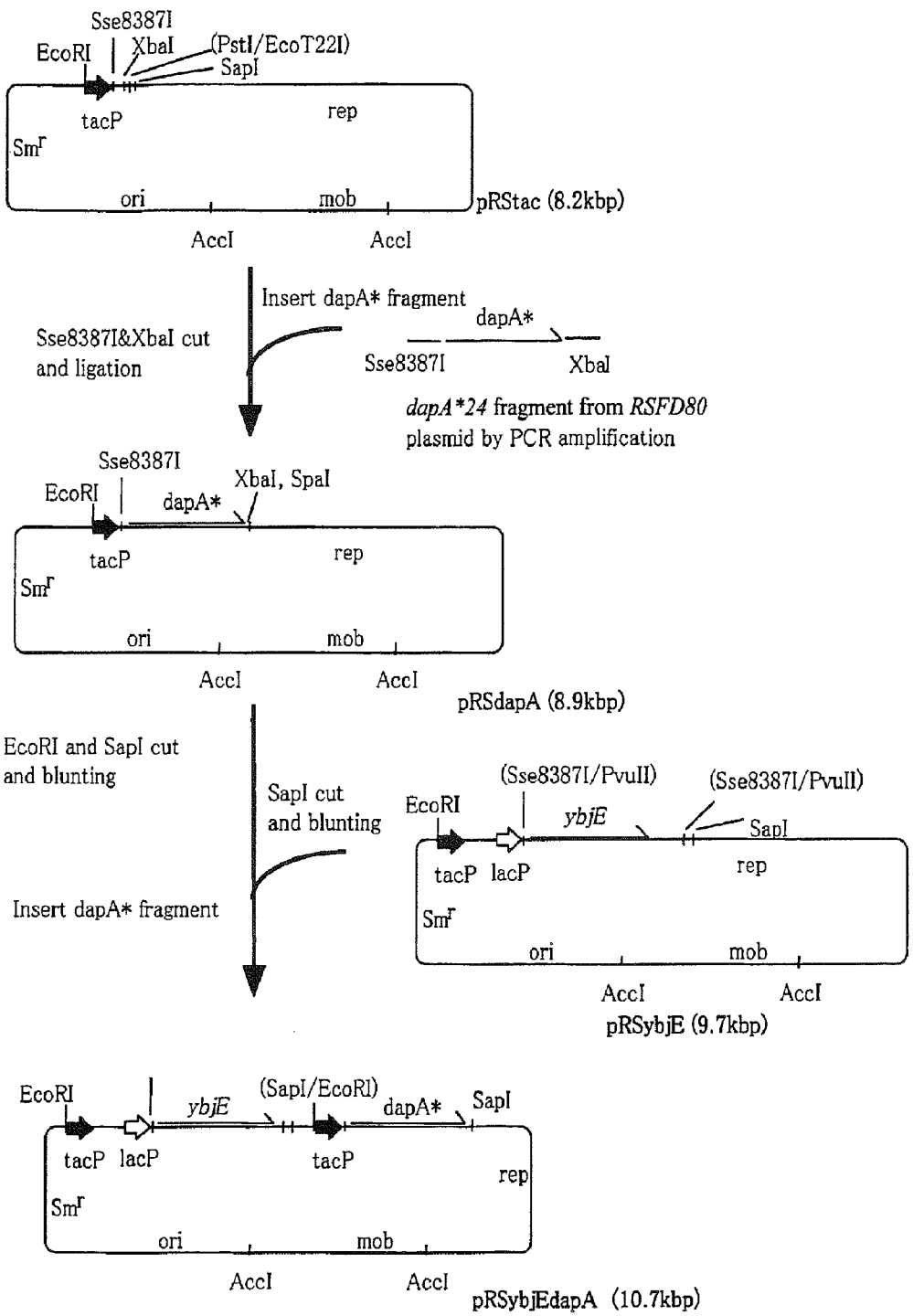
FIG. 5 shows a construction scheme of a plasmid for L-lysine production using methanol-assimilating bacteria.

In order to evaluate the effect of combining ybjE and dapA*, a plasmid obtained by inserting the ybjE gene into pRSdapA plasmid was constructed according to the method shown in FIG. 5. pRSybjE prepared in Example 6 was digested with the restriction enzyme SapI, and blunt-ended using DNA Blunting Kit (Takara Bio). Furthermore, the plasmid pRSdapA was digested with restriction enzymes EcoRI and SapI, and a fragment of about 1 kbp containing the tac promoter and the dapA* region was separated on a 0.8% agarose gel and collected using EASY TRAP Ver. 2 (Takara Bio). This fragment was blunt-ended in the same manner as described above and ligated to the aforementioned digestion product of pRSybjE by using DNA Ligation Kit Ver. 2 (Takara Bio).

This ligation reaction solution was used to transform *Escherichia coli* (*Escherichia coli* JM109 competent cells, Takara Bio). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture by the alkali-SDS method, and the structures of the plasmids were confirmed by digestion with restriction enzymes and DNA sequencing to select pRSybjEdapA plasmid. In this plasmid, the ybjE gene and the dapA* gene were located so that they are transcribed in the same direction relative to each other.

pRSybjEdapA obtained as described above as well as pRSybjE, pRSdapA, and control plasmid pRS were introduced into *Methylophilus methylotrophus* AS1 strain (NCIMB10515) by electroporation, respectively.

<7-3> Production of L-Lysine by *Methylophilus* Bacterium Harboring ybjE and dapA*

Each of the AS1 strains introduced with pRSybjEdapA, pRSybjE, pRSdapA, or pRS, which were obtained as described above, were plated on an SEII plate containing 20 mg/L of streptomycin and cultured overnight at 37° C. Then, the cells from about 0.3 cm² of the medium surface were scraped, inoculated into SEII production medium (20 mL) containing 20 mg/L of streptomycin, and cultured at 37° C. for 34 hours with shaking. After completion of the culture, the cells were removed by centrifugation, and the L-lysine concentration in the culture supernatant was determined by using an amino acid analyzer (Nihon Bunko, high performance liquid chromatography). The results are shown in Table 4. The strain which had been introduced with pRSybjEdapA showed increased L-lysine accumulation compared to the strains introduced only with pRSdapA or pRSybjE. Thus, it was found that enhancing both the ybjE gene and the dapA* gene had a synergistic effect on L-lysine production.

TABLE 4

| Strain | L-Lysine production amount (g/L) |
| --- | --- |
| AS1/pRS | 0.00 |
| AS1/pRSybjE | 0.7 |
| AS1/pRSdapA | 0.12 |
| AS1/pRSybjEdapA | 1.38 |

Example 8

The Effect of ybjE Amplification on Lysine Analogue-Resistance

Figure 6:
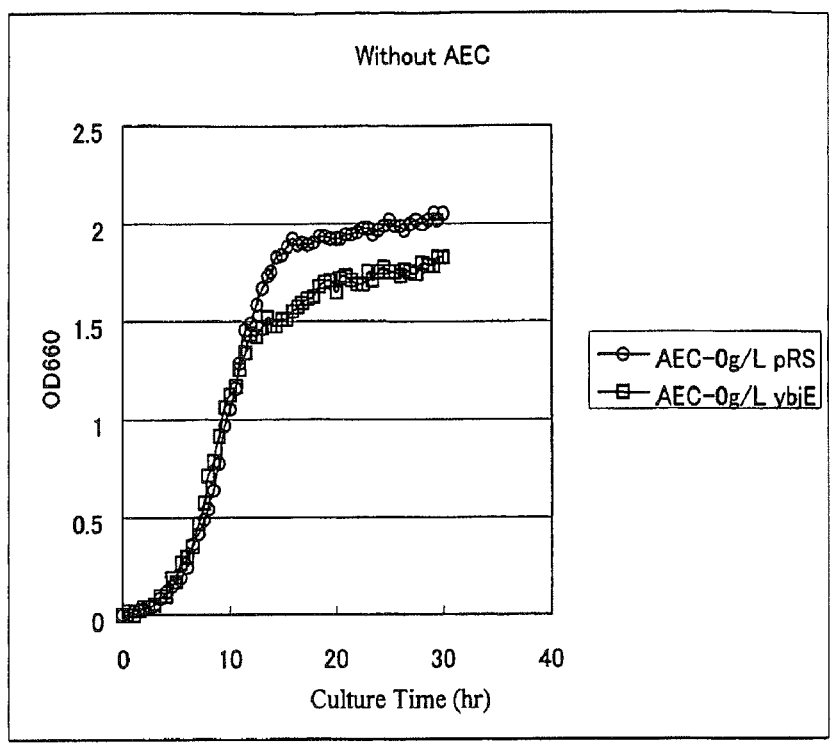
FIG. 6 shows growth curves for a control strain and ybjE gene-amplified strain of *Methylophilus methylotrophus* in the presence of an L-lysine analogue.
Figure 6:
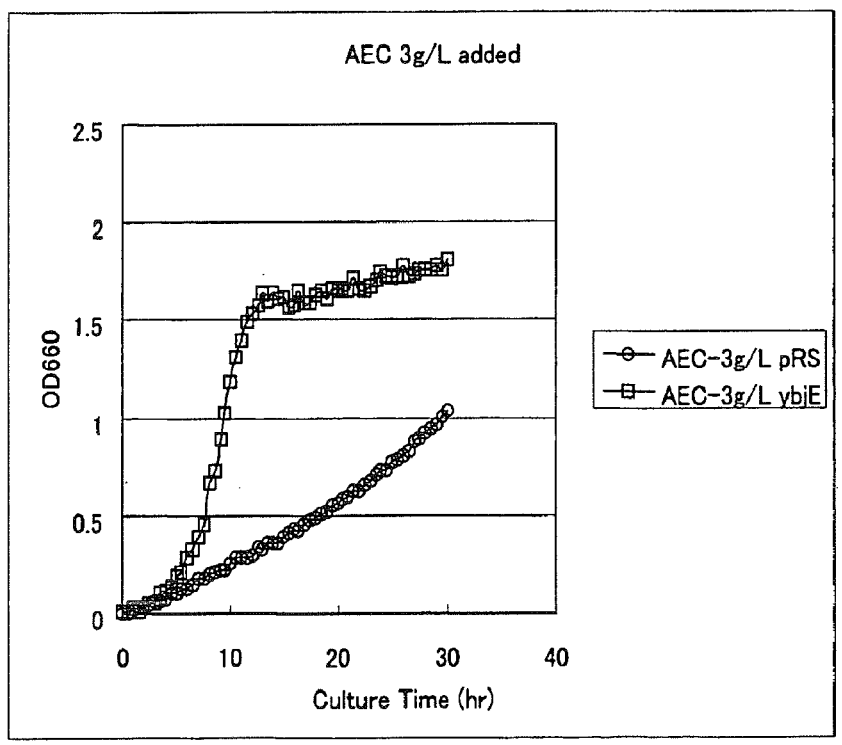
Figure 7:
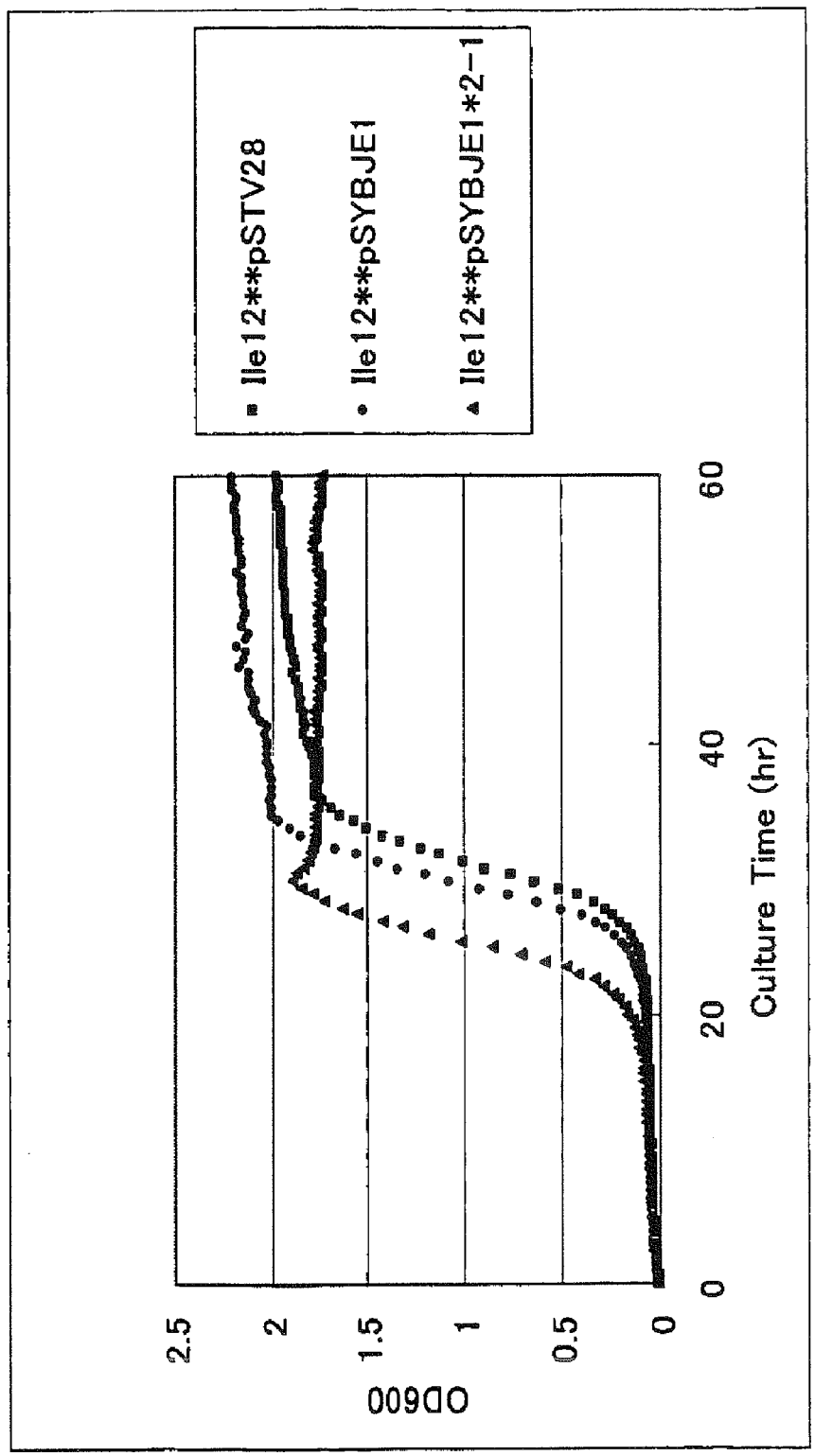
FIG. 7 shows growth curves for a control strain and ybjE gene-amplified strain of *Escherichia coli* in the presence of high concentrations of L-isoleucine.
Figure 8:
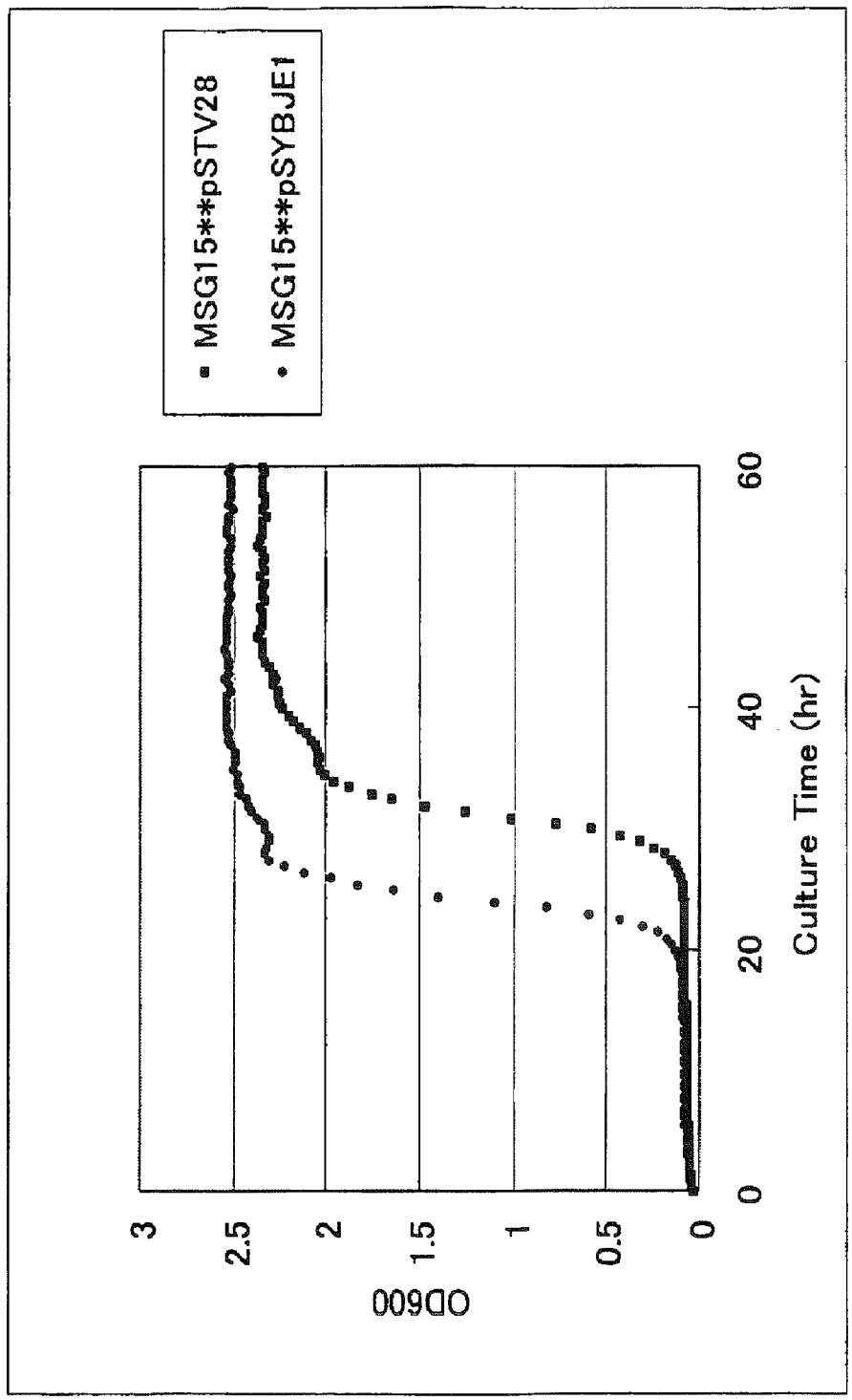
FIG. 8 shows growth curves for a control strain and ybjE gene-amplified strain of *Escherichia coli* in the presence of high concentrations of L-glutamate.
Figure 9:
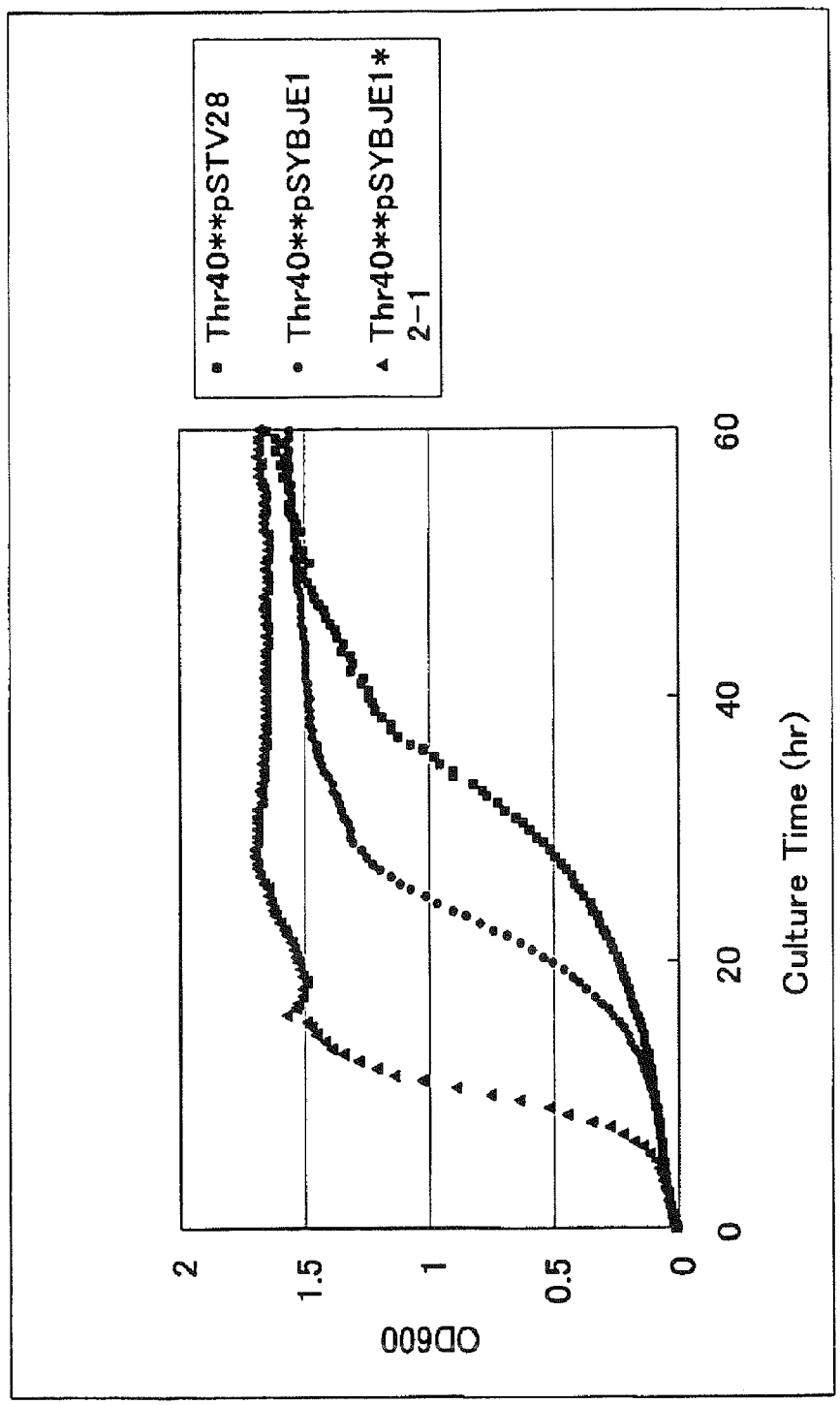
FIG. 9 shows growth curves for a control strain and ybjE gene-amplified strain of *Escherichia coli* in the presence of high concentrations of L-threonine.
Figure 10:
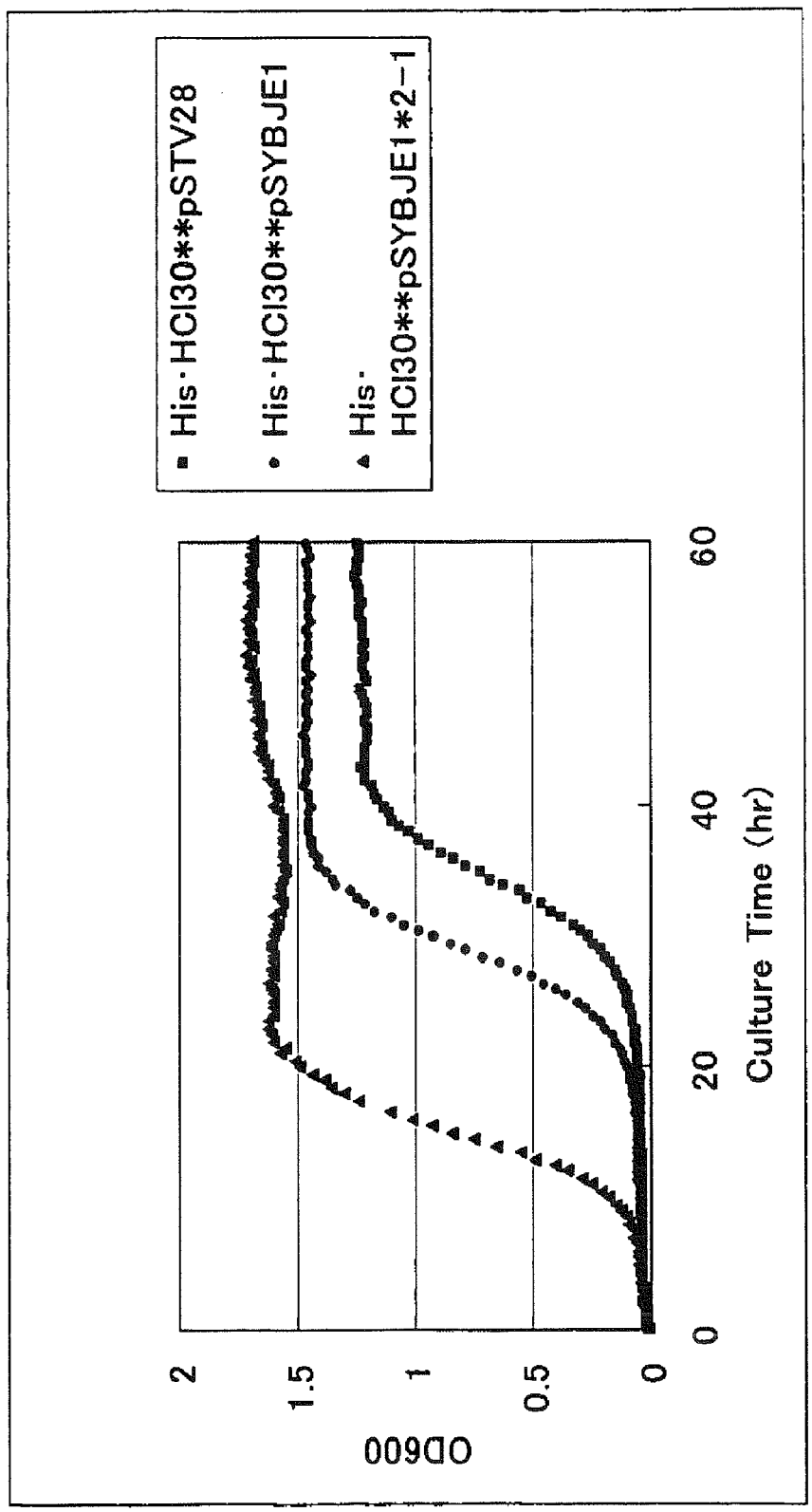
FIG. 10 shows growth curves for a control strain and ybjE gene-amplified strain of *Escherichia coli* in the presence of high concentrations of L-histidine.
Figure 11:
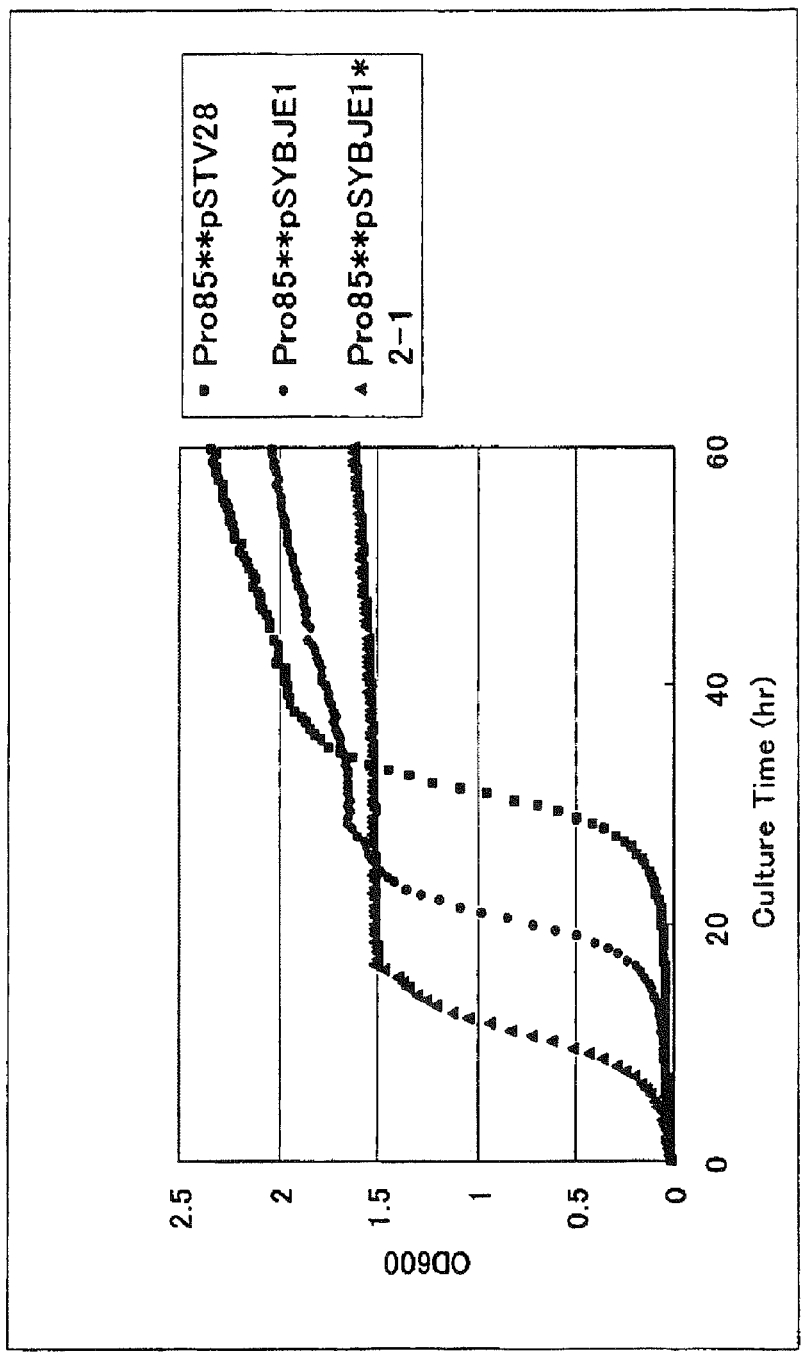
FIG. 11 shows growth curves for a control strain and ybjE gene-amplified strain of *Escherichia coli* in the presence of high concentrations of L-proline.
Figure 12:
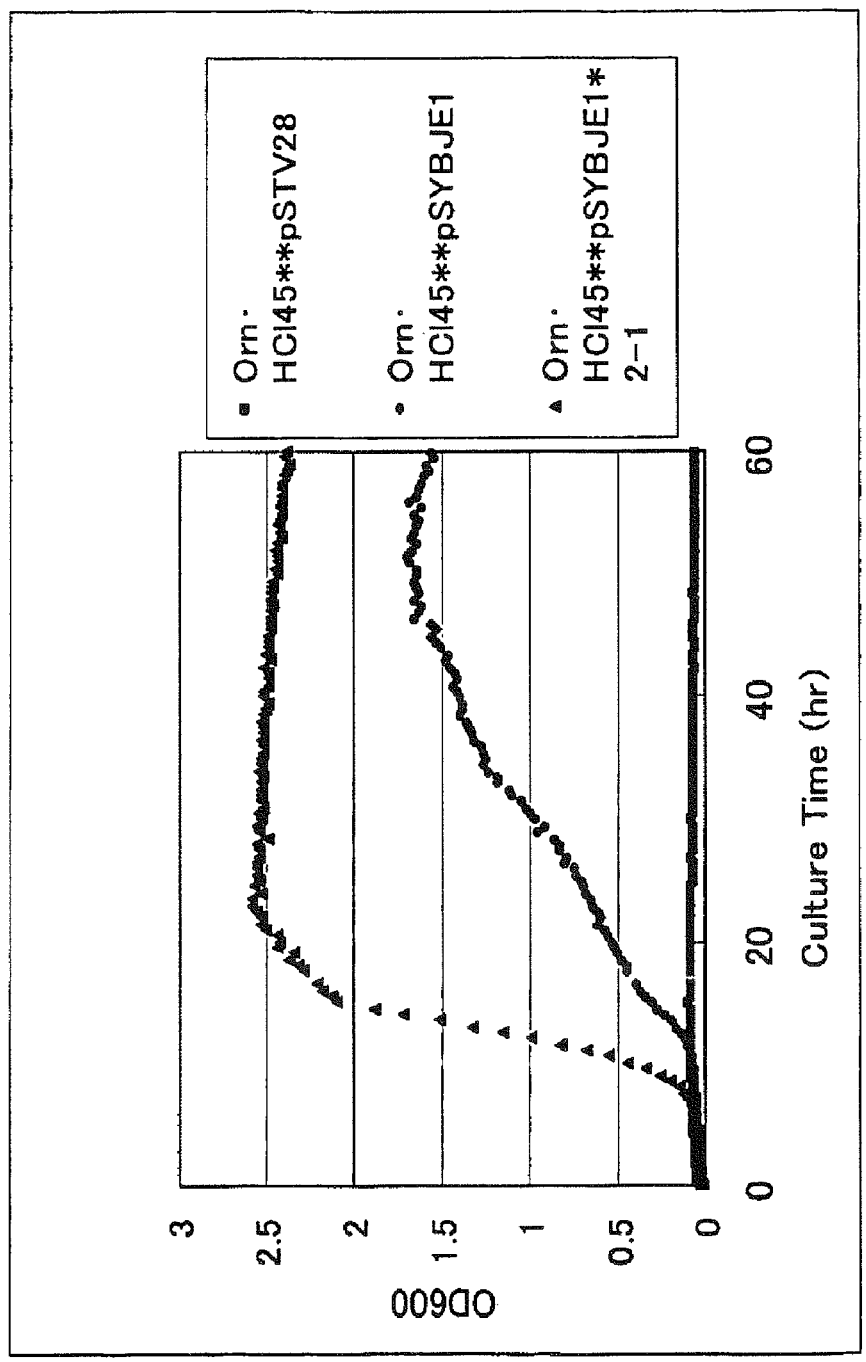
FIG. 12 shows growth curves for a control strain and ybjE gene-amplified strain of *Escherichia coli* in the presence of high concentrations of L-ornithine.
Figure 13:
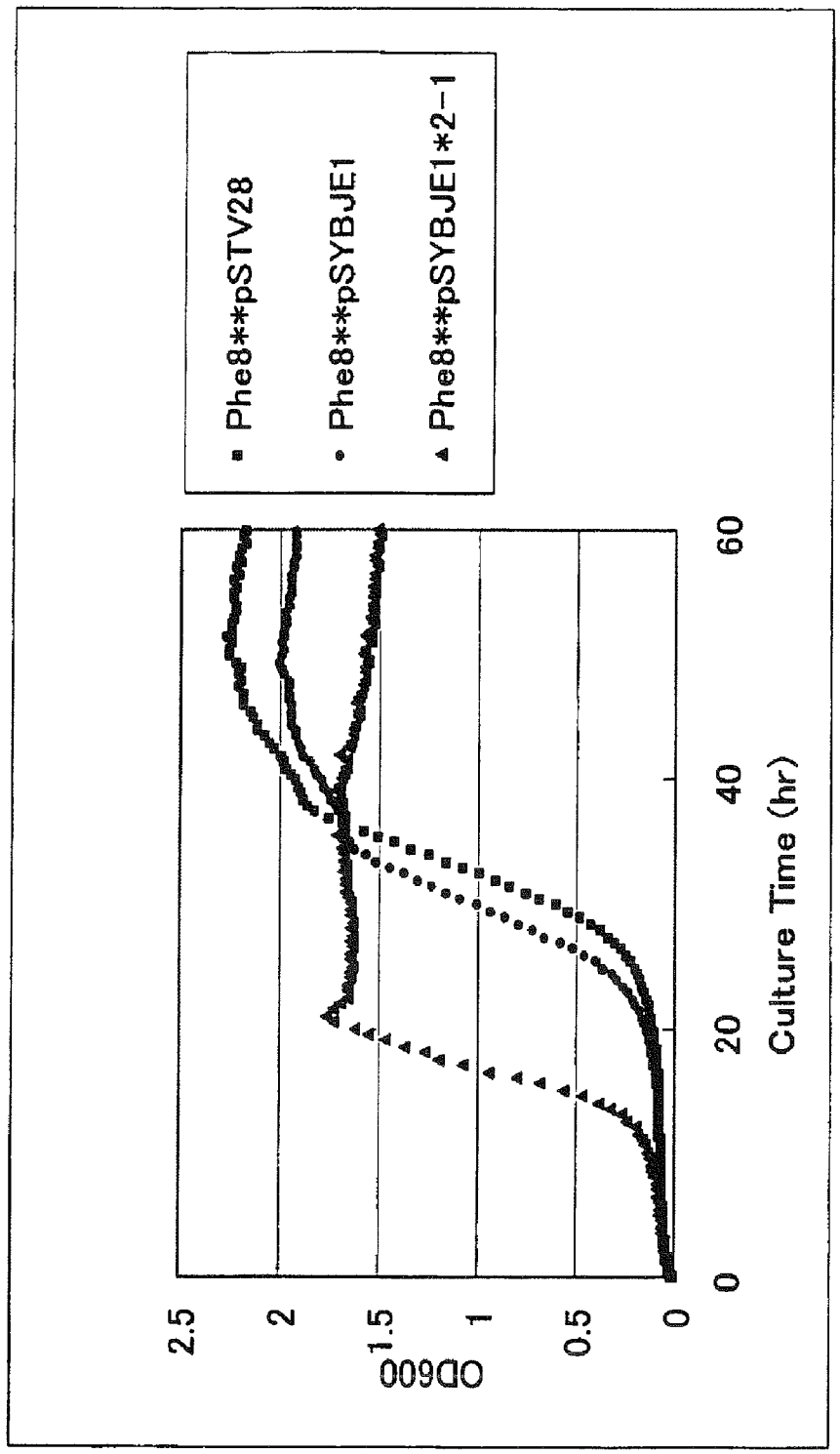
FIG. 13 shows growth curves for a control strain and ybjE gene-amplified strain of *Escherichia coli* in the presence of high concentrations of L-phenylalanine.
Figure 14:
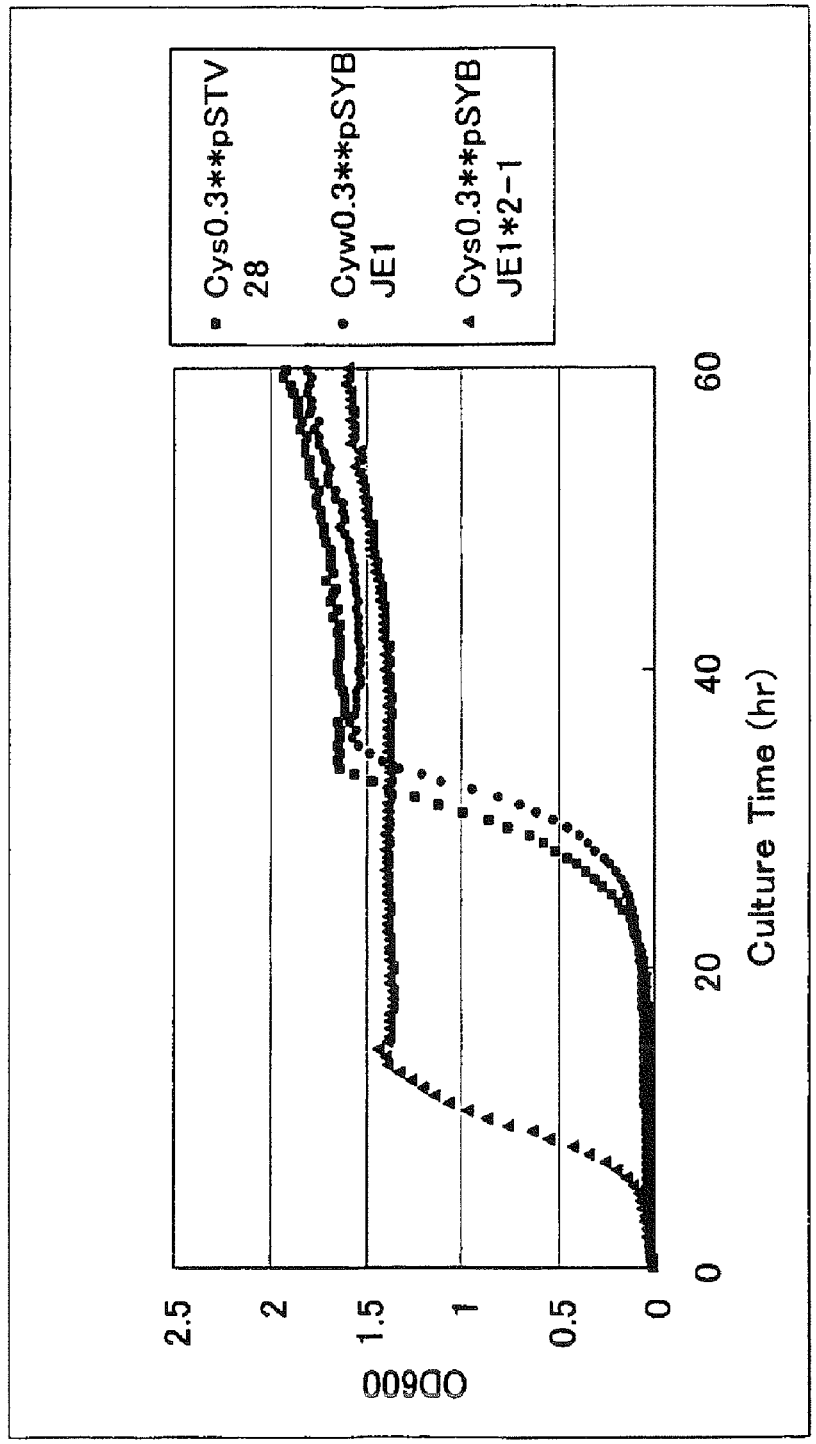
FIG. 14 shows growth curves for a control strain and ybjE gene-amplified strain of *Escherichia coli* in the presence of high concentrations of L-cysteine.
Figure 15:
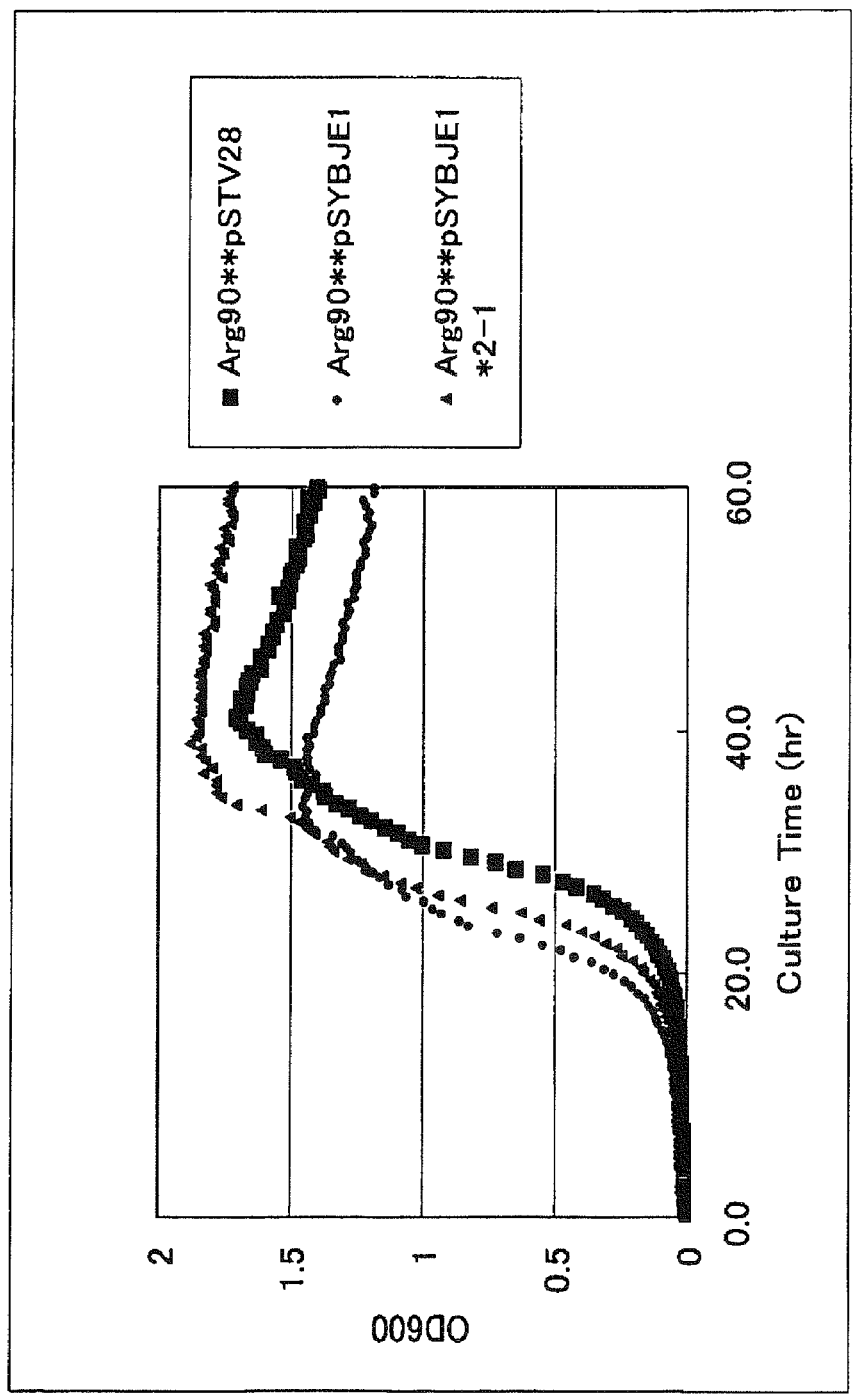
FIG. 15 shows growth curves for a control strain and ybjE gene-amplified strain of *Escherichia coli* in the presence of high concentrations of L-arginine.

Then, the effect of ybjE gene amplification on a lysine analogue-resistance was examined. The aforementioned *Methylophilus methylotrophus* AS1 strains harboring AS1/pRSybjE or control pRS were each cultured overnight in SEII medium containing 20 mg/L of streptomycin. Each culture was inoculated into fresh SEII medium (containing 20 mg/L of streptomycin) in a volume of 10% and cultured at 37° C. with shaking until the cells reached the logarithmic growth phase. Each culture was inoculated in an volume of 4% into SEII medium containing 20 mg/L of streptomycin and 0, 3 or 5 g/L of S-(2-aminoethyl)cysteine (AEC), and cultured at 37° C. with shaking. During the culture, the OD value at 660 nm was measured every 30 minutes to examine the degree of AEC-resistance of the strains. The results are shown in FIG. 6. A biophotorecorder TN-1506 produced by Advantec was used to measure the degree of resistance, and 5 mL of culture was placed into a test tube and analyzed. The results are shown in FIG. 6.

As a result, and with the addition of AEC, no delay of growth was observed for the AS1/pRSybjE strain, whereas the growth of the AS1/pRS strain was markedly delayed. Thus, it was revealed that amplification of the ybjE gene imparted not only L-lysine resistance, but also L-lysine analogue resistance.

Example 9

The Effect of ybjE Amplification on L-Threonine Production

*Escherichia coli* B-5318 strain (EP 0593792) is used as a starting strain. The B-5318 strain is transformed with the plasmid pSYBJE1 as described in Example 2 or a control plasmid pSTV28 (TakaraBio) to obtain a chloramphenicol-resistant strain. After sequence determination, B-5318/pSYBJE1 strain and B-5318/pSTV28 strain can be selected.

These strains are cultured in L-medium containing 50 mg/L of chloramphenicol at 37° C. until OD600 becomes about 0.6. The culture is mixed with the same amount of 40% glycerol solution and divided into portions each having an appropriate volume and stored at −80° C.

The glycerol stock is thawed and 100 µL of it is inoculated uniformly on an L-plate containing 50 mg/L of chloramphenicol and incubated at 37° C. for 24 hours. Then, the cells are collected from about one eighth of the medium surface, inoculated into L-threonine production medium and cultured at 37° C. for 24 hours with shaking. After completion of the culture, the cells are removed by centrifugation, and the L-threonine concentration in the culture supernatant is determined by using a conventional method. Thereby, a strain in which ybjE gene is amplified and has enhanced L-threonine producing ability can be obtained.

Example 10

The Effect of ybjE Gene Amplification in Coryneform Bacterium

<10-1> Construction of a Plasmid for ybjE Gene Amplification pSYBJE2 as described in Example 2 was digested with EcoRI and PstI, and the digested fragment was ligated to pVK7 (US20030175912) which had been digested with the same enzymes. The obtained plasmid was named pVYBJE1.

<10-2> Effect of ybjE Gene Amplification on L-Lysine Production Using Coryneform Bacterium Corynebacterium glutamicum (Brevibacterium lactofermentum) ATCC13861 strain was used as the starting strain. The ATCC13861 strain was transformed with the plasmid pVYBJE1 or a control plasmid pVK7 to obtain a kanamycin-resistant strain. After sequence determination, ATCC13861/pVYBJE1 strain and ATCC13861/pVK7 strain were selected.

These strains were cultured in M-CM2S-medium containing 25 mg/L of kanamycin at 31.5° C. until OD600 became about 0.6. The culture was mixed with an equal amount of 40% glycerol solution and divided into portions each having an appropriate volume and stored at −80° C.

The glycerol stock was thawed and 100 µL was inoculated uniformly on M-CM2S-plate containing 25 mg/L of kanamycin, and incubated at 31.5° C. for 24 hours. Then, the cells were collected from about one eighth of the medium surface, inoculated into 20 ml of fermentation medium containing 25 mg/L of kanamycin and cultured at 31.5° C. for 42 hours with shaking at 115 rpm. After completion of the culture, the cells were removed by centrifugation, and the L-lysine concentration in the culture supernatant is determined using a Biotech Analyzer AS210 (Sakura Seiki). All the glucose in the medium had been completely consumed after culturing for 42 hours.

The results are shown in Table 5. ATCC13861/pVYBJE1 in which ybjE gene is amplified was able to cause accumulation of L-lysine in a higher amount as compared to the control ATCC13861/pVK7 strain. It was found that ybjE gene also functions in L-amino acid export and enhances L-lysine production in Coryneform bacterium.

TABLE 5

| Strain | Production amount of L-lysine (g/L) |
| --- | --- |
| ATCC13861/pVK7 | 1.1 |
| ATCC13861/pVYBJE1 | 4.2 |

Example 11

The Effect of ybjE Gene Amplification on Growth Under High Concentrations of L-Amino Acids Escherichia coli MG1655 strain (ATCC47076) was transformed with pSYBJE1 including ybjE gene or control plasmid pTSV28 (TakaraBio). In addition, MG1655 strain was also transformed with pSYJE1*2-1 including a mutant ybjE gene having a sequence of SEQ ID NO: 1 in which the nucleotide (guanine) at the $3^{rd}$ position is replaced with adenine.

Transformants introduced with these plasmids were selected according to chloramphenicol-resistance and the selected strains were named MG1655/pSYJE1, MG1655/pSYJE1*2-1, and MG1655/pSTV28, respectively.

pSYJE1*2-1 was constructed as follows. Mutant ybjE gene was amplified by PCR using primers each having a sequence of SEQ ID NOS: 5 or 6 from a chromosomal DNA of the L-lysine-producing NVC578 strain of E. coli. The amplified DNA was sequenced and found to have a sequence of SEQ ID NO: 1 in which the nucleotide (guanine) at the $3^{rd}$ position is replaced with adenine. The amplified DNA was ligated with SmaI-digested pTV28 and a plasmid in which the mutant ybjE gene was placed so that it was expressed by a lac promoter was selected and named pSYJE1*2-1.

The mutant ybjE gene may also be obtained by introducing the mutation into a wild-type ybjE gene using methods such as overlap-extension PCR (Nucleic Acids Res, 25, 2227-8. 1997), in which mutant ybjE gene is amplified with primers one of which has the nucleotide replacement.

Then, growth of MG1655/pSYJE1, MG1655/pSYJE1*2-1, and MG1655/pSTV28 strains in the presence of high concentrations of each L-amino acid was examined.

These strains were cultured with shaking in 5 ml of L-medium containing 50 mg/L of chloramphenicol for about 6 hours. After OD600 of the medium reached about 1.0, the culture was centrifuged and cells were washed twice with M9 minimum medium and inoculated at OD600=0.05 into M9 minimum medium containing 50 mg/L of chloramphenicol and each L-amino acid (12 g/L isoleucine, 40 g/L threonine, 15 g/L sodium glutamate, 30 g/L histidine hydrochloride, 45 g/L ornithine hydrochloride, 90 g/L arginine hydrochloride, 8 g/L phenylalanine, 85 g/L proline or 0.3 g/L cysteine), and cultured for 70 hours. L-isoleucine was chosen as a representative of aliphatic L-amino acids, L-threonine was chosen as a representative of hydroxyl L-amino acids, L-proline was chosen as a representative of circular L-amino acids, L-phenylalanine was chosen as a representative of aromatic L-amino acids, L-cysteine was chosen as a representative of sulfur-containing L-amino acids, L-glutamic acid was chosen as a representative of acidic L-amino acids and their amides.

The results are shown in FIGS. 7-15. It was found that ybjE gene amplification improved the growth of MG1655 strain in the presence of high concentrations of L-amino acids, especially L-arginine, L-ornithine, L-isoleucine, L-glutamic acid, L-threonine, L-histidine, L-proline, L-phenylalanine, and L-cysteine. It was also found that the mutant ybjE gene confers amino acid resistance to the MG1655 strain more efficiently than the wild-type ybjE gene.

Example 12

Effect of the ybjE Gene Having a Nucleotide Sequence of Nucleotide Numbers 49-948 of SEQ ID NO: 1

The ybjE gene, which has a nucleotide sequence of nucleotide numbers 49-948 of SEQ ID NO: 1 (referred to as ybjE- 900 hereinafter) was amplified from a chromosomal DNA of the MG1655 strain by PCR using primers having a nucleotide sequence of SEQ ID NO: 13 or 12. The ybjE gene having a nucleotide sequence of nucleotide numbers 1-948 of SEQ ID NO: 1 in which guanine at position 1 is replaced with adenine (referred to as ybjE-948 hereinafter) was also amplified by PCR using primers having a nucleotide sequence of SEQ ID NO: 11 or 12.

The PCR product obtained from each reaction was purified and each ligated to a SmaI-digested pTV28 vector (Takara Bio), thereby obtaining a plasmid for amplifying ybjE-900 gene or ybjE-948 gene. A plasmid in which the ybjE-900 gene was placed so be expressed by the lac promoter was selected and named pSYBJE900, and a plasmid in which ybjE-948 gene was placed to be expressed by the lac promoter was selected and named pSYBJE948.

*Escherichia coli* MG1655 strain (ATCC47076) was transformed with pSYBJE900, pSYBJE948, pSYBJE1 used in Example 2, or control plasmid pSTV28. Transformants introduced with these plasmids were selected according to chloramphenicol-resistance and the selected strains were named MG1655/pSYBJE900, MG1655/pSYBJE948, MG1655/pSYJE1 and MG1655/pSTV28, respectively.

Then, the growth of MG1655/pSYBJE900, MG1655/pSYBJE948, MG1655/pSYJE1, and MG1655/pSTV28 strains in the presence of high concentrations of L-lysine was examined.

These strains were cultured with shaking in 3 ml of L-medium containing 50 mg/L of chloramphenicol for about 6 hours. After OD600 of the medium became about 1.0, the culture was centrifuged and cells were washed twice with M9 minimum medium and inoculated at OD600=0.05 into M9 minimum medium containing 50 mg/L of chloramphenicol and 80 g/L of lysine hydrochloride, and cultured for about 20 hours.

Figure 16:
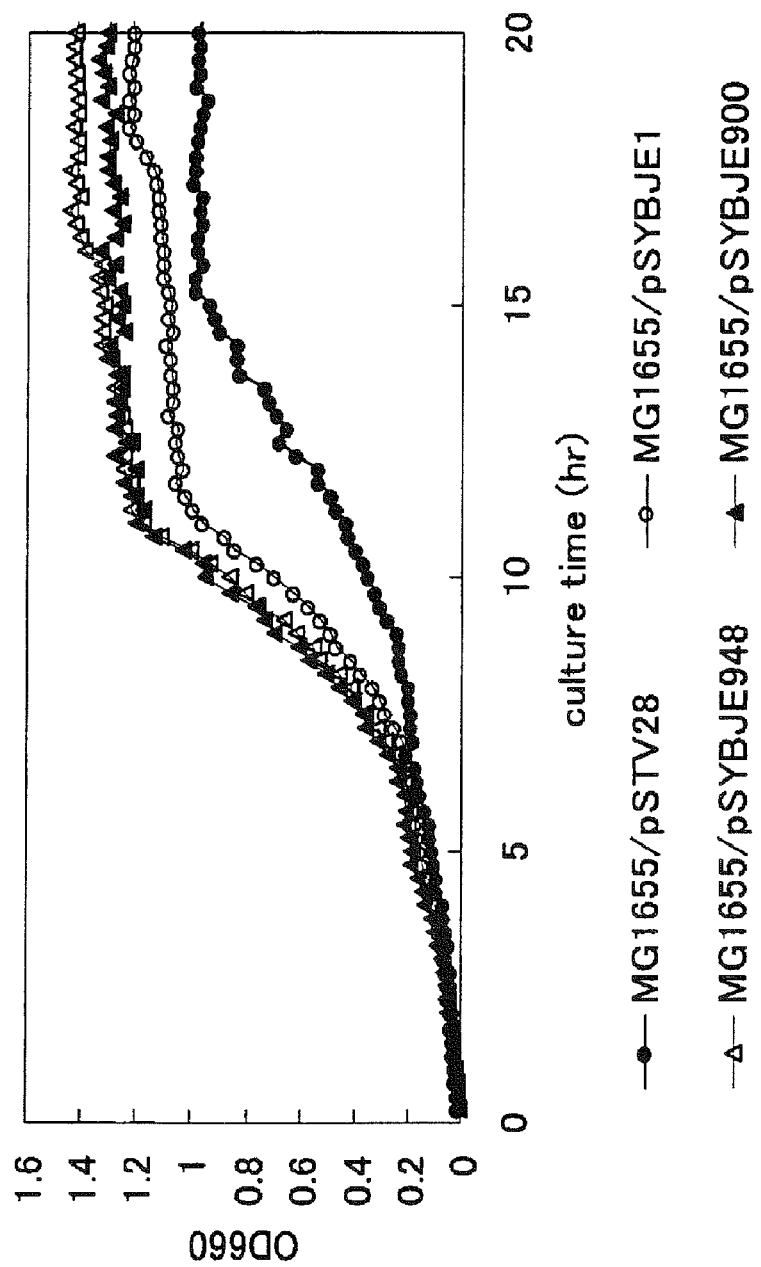
FIG. 16 shows growth curves of a control strain and ybjE gene (948 bp or 900 bp)-amplified strains of *Escherichia coli* in the presence of high concentrations of L-lysine.

The results are shown in FIG. 16. It was found that amplification of the ybjE-900 gene improves growth of the MG1655 strain in the presence of high concentrations of L-lysine in the early growth phase as well as in the log growth phase to almost the same extent as the ybjE-948 and ybjE genes contained in pSYJE1. These data suggested that a sequence of nucleotide numbers 49-948 in the sequence of ybjE gene (SEQ ID NO: 1) is sufficient to exert its L-amino acid-export effect.

INDUSTRIAL APPLICABILITY

According to the present invention, L-amino acids, especially L-lysine, L-threonine, L-isoleucine, L-proline, L-arginine, L-ornithine, L-histidine, L-phenylalanine, and L-glutamic acid can be efficiently produced by fermentation. L-lysine, L-threonine, L-isoleucine and L-proline are useful as additives for animal feed, components of health food, and amino acid infusions. L-arginine and L-ornithine are useful as liver function-promoting agents, amino acid infusions, and components of comprehensive amino acid preparations. L-histidine is useful as a liver function-promoting agent and a precursor of histamine. L-phenylalanine is useful as a precursor of sweeteners.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP2004-023347, is incorporated by reference herein in its entirety.

What is claimed is:

1. A method for producing a basic L-amino acid comprising:
   A) culturing an *Escherichia coli* bacterium in a medium, and
   B) collecting said basic L-amino acid from the medium and/or the bacterium, wherein said bacterium has been modified to have enhanced expression of a ybjE gene as compared to a non-modified *Escherichia coli* bacterium, and wherein said ybjE gene encodes a protein which is 95% or more homologous to an amino acid sequence selected from the group consisting of:
   a) the entire amino acid sequence of SEQ ID NO: 2, and
   b) the amino acid sequence of numbers 17 to 315 of SEQ ID NO: 2;

and wherein said protein imparts the ability to said *Escherichia coli* bacterium to export a basic L-amino acid, and
   wherein the enhanced expression of said ybjE gene is obtained by a method selected from the group consisting of:
   i) increasing the copy number of said ybjE gene,
   ii) replacing a promoter of said ybjE gene with a stronger promoter, and
   iii) combinations thereof.

2. The method according to claim 1, wherein said ybjE gene encodes a protein which has the amino acid sequence of SEQ ID NO: 2.

3. A method for producing a basic L-amino acid comprising:
   A) culturing an isolated *Escherichia coli* bacterium in a medium, and
   B) collecting the basic L-amino acid from the medium and/or the bacterium, wherein said bacterium comprises a ybjE gene which comprises the DNA sequence of SEQ ID NO: 1, except that the guanine at the $3^{rd}$ position is replaced by adenine.

4. The method according to claim 1, wherein said basic L-amino acid is L-lysine.

5. The method according to claim 1, wherein said basic L-amino acid is L-arginine.

6. A method for producing a basic L-amino acid comprising:
   A) culturing an *Escherichia coli* bacterium in a medium, and
   B) collecting said basic L-amino acid from the medium and/or the bacterium, wherein said bacterium has been modified to have enhanced expression of a ybjE gene as compared to a non-modified *Escherichia coli* bacterium, and wherein said ybjE gene encodes a protein which is 95% or more homologous to an amino acid sequence selected from the group consisting of:
   a) the entire amino acid sequence of SEQ ID NO: 2, and
   b) the amino acid sequence of numbers 17 to 315 of SEQ ID NO: 2;

and wherein said protein imparts the ability to said *Escherichia coli* bacterium to export a basic L-amino acid, and
   wherein the enhanced expression of said ybjE gene is obtained by replacing a promoter of said ybjE gene with a tac promoter.

7. The method according to claim 6, wherein said basic L-amino acid is L-lysine.

8. The method according to claim 6, wherein said basic L-amino acid is L-arginine.

9. The method according to claim 3, wherein said basic L-amino acid is L-lysine.

10. The method according to claim 3, wherein said basic L-amino acid is L-arginine.

* * * * *